(12) United States Patent
Tarafder

(10) Patent No.: US 10,578,592 B2
(45) Date of Patent: Mar. 3, 2020

(54) METHOD FOR ESTIMATING TEMPERATURE VARIATION IN CHROMATOGRAPHY USING THERMODYNAMIC PLOTS AND USES THEREOF

(71) Applicant: Waters Technologies Corporation, Milford, MA (US)

(72) Inventor: Abhijit Tarafder, Franklin, MA (US)

(*) Notice: Subject to any disclaimer, the term of this patent is extended or adjusted under 35 U.S.C. 154(b) by 456 days.

(21) Appl. No.: 15/310,539

(22) PCT Filed: May 12, 2015

(86) PCT No.: PCT/US2015/030244
§ 371 (c)(1),
(2) Date: Nov. 11, 2016

(87) PCT Pub. No.: WO2015/175447
PCT Pub. Date: Nov. 19, 2015

(65) Prior Publication Data
US 2017/0082583 A1 Mar. 23, 2017

Related U.S. Application Data

(60) Provisional application No. 61/992,061, filed on May 12, 2014, provisional application No. 61/992,016, filed on May 12, 2014.

(51) Int. Cl.
*G01N 30/30* (2006.01)
*G01N 30/02* (2006.01)

(52) U.S. Cl.
CPC ....... *G01N 30/30* (2013.01); *G01N 2030/025* (2013.01); *G01N 2030/027* (2013.01)

(58) Field of Classification Search
CPC ............. G01N 30/30; G01N 2030/025; G01N 2030/027
USPC ......................................................... 73/23.26
See application file for complete search history.

(56) References Cited

U.S. PATENT DOCUMENTS

2009/0320660 A1   12/2009   Gwosdz-Kaupmann et al.

FOREIGN PATENT DOCUMENTS

WO       2014008058       1/2014

OTHER PUBLICATIONS

Tarafder, Abhijit, et al., "Use of Isopycnic Plots in Designing Operations of Supercritical Fluid Chromatography III. Reason for the Low Column Efficiency in the Critical Region", Journal of Chromatography A, (2011), vol. 1218, Issue 40, pp. 7189-7195.

(Continued)

*Primary Examiner* — Tarun Sinha
(74) *Attorney, Agent, or Firm* — Womble Bond Dickinson (US) LLP; Deborah M. Vernon; Heath T. Misley

(57) ABSTRACT

A method for estimating temperature variation due to pressure drop in a mobile phase passing through a column in a high efficiency chromatographic separation system is provided. The method includes constructing a temperature triangle using a pressure-temperature thermodynamic plot of the mobile phase having isenthalpic curves of the mobile phase. Applications of the method include development of chromatographic methods for minimizing band broadening due to temperature variation and methods to mitigate the extent of temperature variation due to the pressure drop.

12 Claims, 24 Drawing Sheets

Axial temperature variation

Radial temperature variation

(56) References Cited

OTHER PUBLICATIONS

Tarafder, Abhijit, et al., "Use of Isopycnic Plots in Designing Operations of Supercritical Fluid Chromatography II. The Isopycnic Plots and the Selection of the Operating Pressure—Temperature Zone in Supercritical Fluid Chromatography", Journal of Chromatography A, (2011) vol. 1218, Issue 28, pp. 4576-4585.

Kaczmarski, Krzysztof, et al., "Modeling of Thermal Processes in High Pressure Liquid Chromatography II. Thermal Heterogeneity at Very High Pressures", Journal of Chromatography A, (2009), vol. 1216, pp. 6575-6586.

Poppe, H., et al., "Temperature Gradients in HPLC Columns Due to Viscous Heat Dissipation", Chromatographia, Sep. 1981, vol. 14, No. 9, pp. 515-523.

Gritti, Fabrice, et al., "Effects of the Thermal heterogeneity of the Column on Chromatographic Results", Journal of Chromatography A, (2006), vol. 1131, pp. 151-165.

Poe, Donald P., et al., "Effects of Pressure Drop, Particle Size and Thermal Conditions on Retention and Efficiency in Supercritical Fluid Chromatography", Journal of Chromatography A, (2009), vol. 1216, pp. 7915-7926.

Kaczmarski, Krzysztof, et al., "Modeling of Thermal Processes in Highly Pressure Liquid Chromatography I. Low Pressure Onset of Thermal Heterogeneity", Journal of Chromatography A., (2009), vol. 1216, pp. 6560-6574.

Kaczmarski, Krzysztof, et al., "Numerical Modeling of Elution Peak Profiles in Supercritical Fluid Chromatography. Part I—Elution of an Unretained Tracer", Journal of Chromatography A, (2010), vol. 1217, pp. 6578-6587.

Tarafder, Abhijit, et al., "Estimations of Temperature Deviations in Chromatographic Columns Using Isenthalpic Plots. I. Theory for Isocratic Systems", Journal of Chromatography A, (2014), vol. 1366, pp. 126-135.

Poe, Donald P., et al., "Pressure, Temperature and Density Drops Along Supercritical Fluid Chromatography Columns in Different Thermal Environments. III. Mixtures of Carbon Dioxide and Methanol as the Mobile Phase", Journal of Chromatography A, (2014), vol. 1323, p. 143-156.

Transmittal of International Search Report, based on International Application No. PCT/US2015/30244, dated Jul. 28, 2015, 4 Pages.

Written Opinion based on International Application No. PCT/US2015/30244, dated Jul. 28, 2015, 5 Pages.

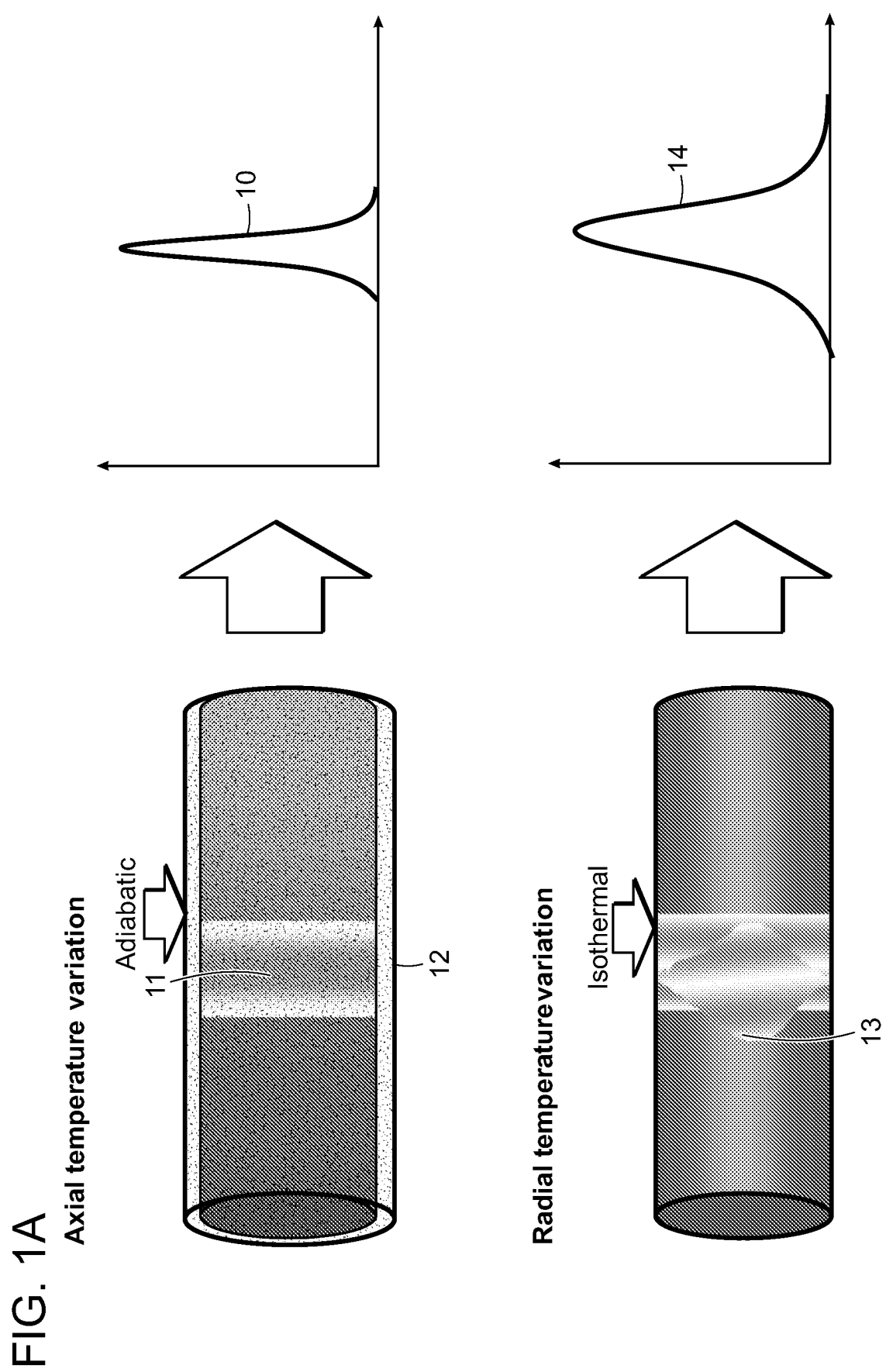

METHOD FOR ESTIMATING TEMPERATURE VARIATION IN CHROMATOGRAPHY USING THERMODYNAMIC PLOTS AND USES THEREOF

CROSS-REFERENCE TO RELATED APPLICATIONS

This application is a National Stage Application of International Application No. PCT/US2015/030244 filed May 12, 2015, which claims priority to U.S. Provisional Application No. 61/992,016 filed May 12, 2014, and U.S. Provisional Application No. 61/992,061 filed May 12, 2014, each of which is incorporated herein by reference in its entirety.

TECHNICAL FIELD

The present disclosure relates to methods for rapidly estimating temperature variation in high-efficiency chromatography using thermodynamic parameters of the mobile phase.

BACKGROUND OF THE INVENTION

High-efficiency, high throughput chromatography has greatly advanced the analysis of complex chemical and biological mixtures. The ability of a chromatographic column to separate the various components present in a complex multi-component mixture heavily depends on the efficiency of the column. Column efficiency, in turn, is largely controlled by particle size of the material forming the chromatographic bed. The lower the particle size, the higher the column efficiency. As a result, with time, the particle size for chromatographic separation has become progressively smaller.

An important factor for achieving higher throughput chromatographic separation is short run time. This requires the mobile phase to be passed through the column at a high flow rate. The combination of low particle size and high flow rate leads to significant pressure drop in the mobile phase throughout the length of the chromatographic column. The extent of the pressure drop depends on the viscosity of the mobile phase. Pressure drop in the mobile phase requires use of pumps that can push the mobile phase into the column with greater and greater force. As a result, chromatographic instruments have continuously evolved to incorporate both smaller particles and high flow rates as exemplified by the development of Ultra High Performance Liquid Chromatography (or UHPLC) instruments that are capable of forcing the mobile phase at much higher flow rates compared to the traditional High Performance Liquid Chromatography (HPLC) instruments.

Pressure drop in the mobile phase is accompanied with a rise in the temperature of the mobile phase due to increased friction between the mobile phase and the particles of the chromatographic bed. The larger the pressure drop, the greater the extent of temperature rise. In most situations neither the mobile phase nor the chromatographic bed is sufficiently thermally conductive to equilibrate the temperature rise uniformly from the interior of the column to the areas closest to the column wall. The mobile phase near the wall can dissipate the frictional heat more easily through the wall and therefore can maintain a temperature closer to the temperature set by a column oven. If the column is not in contact with a heater (i.e., it is kept in the open under ambient temperature), it maintains a temperature closer to the ambient temperature. However, the mobile phase along the column central axis (i.e., lengthwise along center of column) fails to reach the temperature of the mobile phase near the wall. The temperature difference results in a radial thermal gradient. A thermal gradient in the radial direction, in general, reduces column efficiency due to band broadening.

Similar thermal effects are also observed in $CO_2$-based chromatography when high flow rates and lower particle sizes are employed. However, the immediate physical consequences that ultimately lead to band broadening in $CO_2$-based chromatography are different from those observed in UHPLC. In $CO_2$-based chromatography, because of the significant concentration of $CO_2$ in the mobile phase, the viscosity of the mobile phase is much lower. Lower viscosity considered alone should result in a smaller pressure drop, and therefore, less temperature variation in the radial direction in comparison to UHPLC. However, unlike UHPLC, pressure drop in $CO_2$-based chromatography leads to significant mobile phase expansion, which in turn produces a cooling effect. The net result is that the temperature of the mobile phase near the wall is higher than that along central axis of the column.

Although it is well known that operation of both UHPLC and $CO_2$-based chromatography is associated with temperature variation and resultant loss in column performance, the extent to which the temperature varies is not readily estimated by current methods. In this regard, $CO_2$-based chromatography is more complex compared to UHPLC, because in $CO_2$-based chromatography the physical properties of the mobile phase can vary significantly as a function of the operating pressure and temperature (as compared to liquids in UHPLC, due to significant changes in density). Consequently widely different temperature variations may be experienced along the column during $CO_2$-based chromatography, depending on the selection of operating pressure and temperature.

Temperature variation aspects of both UHPLC and $CO_2$-based chromatography systems have been examined experimentally and through simulation studies. For example, see Kaczmarski, et al., (2009) *J. Chromatogr. A*, 1216 (38), pp. 6575-6586, and Kaczmarski, K., (2010) *J. of Chromatogr. A*, 1217 (42), pp. 6578-6587, which are incorporated herein by reference in their entireties. Although these studies have generated useful insight into the nature of the temperature variation, the methods employed to estimate the variation have been complex, and therefore, not helpful in most practical situations.

SUMMARY OF THE INVENTION

Exemplary embodiments of the present technology are directed to methods for conveniently estimating the extent of temperature variation associated with pressure drop in a mobile phase during high-efficiency liquid chromatography (e.g., UHPLC at high pressures or $CO_2$-based chromatography). Additional methods are described that utilize this information for developing chromatographic separation methods, or for improving the resolution of one or more analyte peaks in a chromatographic separation. These methods can involve selecting a mobile phase that exhibits lower temperature variation, or pre-heating or pre-cooling the mobile phase, or using heat exchangers at various positions in the chromatography column or combinations thereof. Further, methods are also provided that utilize the temperature variation information for determining a mobile phase composition which can maintain density and temperature at substantially constant levels as pressure varies.

In accordance with the embodiments of the present disclosure a method for estimating temperature variation of a mobile phase passing through a column in a chromatographic separation system is disclosed. The method includes the steps of providing a pressure-temperature (P-T) phase diagram of the mobile phase, such that the phase diagram includes isenthalpic curves of the mobile phase; drawing a triangular figure by connecting a first, second, and a third point on the phase diagram, such that the first point corresponds to the temperature of the column $T_{first}$, and the mobile phase pressure $P_{first}$ at a first position in the column; the second point corresponds to $T_{first}$, and to the mobile phase pressure $P_{second}$ at a second position in the column; and the third point corresponds to $P_{second}$, and $T_{second}$, such that $T_{second}$ is the temperature of the mobile phase at the second position, such that the first and the third points lie on the same isenthalpic curve; and estimating the temperature variation by calculating the difference between $T_{first}$ and $T_{second}$. The triangular figure is referred to as a temperature triangle.

Embodiments of the above exemplary method can include one or more of the following features. In some embodiments the second position is downstream from the first position. In related embodiment, $P_{first}$ and $P_{second}$, respectively, are the pressures of the mobile phase, and $T_{first}$ and $T_{second}$ are the temperatures of the mobile phase at the entry point and the exit point, respectively, of the column. In various embodiments the system includes an ultra-high performance liquid chromatography system, a $CO_2$-based chromatography system, a high temperature liquid chromatography system, or a chromatography system that uses sub-critical or supercritical fluid as the mobile phase.

In accordance with another embodiment of the present technology, a method of developing a chromatographic separation process is disclosed. The method includes the steps of selecting a column and a first mobile phase composition; estimating temperature variation in the first mobile phase composition between pressures $P_{inlet}$ and $P_{outlet}$ using the temperature triangle described above, such that $P_{inlet}$ and $P_{outlet}$, respectively, are the pressures of the mobile phase at the entry point and at the exit point of the column; and determining a second mobile phase composition for the process, such that the estimated temperature variation in the second mobile phase composition between $P_{inlet}$ and $P_{outlet}$ is different from that in the first mobile phase composition.

Embodiments of the above exemplary method of developing a chromatographic separation process can include one or more of the following features. In various embodiments the chromatographic separation process is performed using an ultra-high performance liquid chromatography system, or a $CO_2$-based chromatography system, or a high temperature liquid chromatography system, or a chromatography system that uses sub-critical or supercritical fluid as the mobile phase. In another embodiment the estimated temperature variation for the second mobile phase is smaller than that in for the first mobile phase.

In accordance with a further embodiment of the present technology, a method for improving resolution of one or more analyte peaks in a chromatographic separation process is disclosed. The method includes the steps of estimating, using the temperature triangle above, temperature variation in the mobile phase, a first mobile phase, due to a pressure drop; and obtaining a reduction in width of at least one of the one or more analyte peaks by substituting the first mobile phase with a second mobile phase having a composition different from that of the first, such that temperature variation in the second mobile phase due to the pressure drop, estimated using the temperature triangle described above, is different compared to that estimated for the first mobile phase. In related embodiments, the estimated temperature variation in the second mobile phase is smaller than that estimated for the first mobile phase.

Further, in accordance with embodiments of the present technology another method for improving resolution of one or more analyte peaks in a chromatographic separation process is disclosed. The method includes the steps of providing a column and a mobile phase for the process; estimating temperature variation due to pressure drop in the mobile phase between a first position and a second position in the column, such that the temperature variation is estimated using the temperature triangle described above; and pre-cooling or pre-heating the mobile phase by a temperature equal to or less than the temperature variation estimated using the temperature triangle described above.

In accordance with the embodiments of the present technology an additional method for improving resolution of one or more analyte peaks in a chromatographic separation process is disclosed. The method includes the steps of providing a column and a mobile phase; estimating temperature variation due to pressure drop in a first mobile phase between a first position and a second position in the column; and cooling or heating the column at one or more positions along the length of the column during the separation process, such that the cooling or heating results in a smaller temperature variation in the mobile phase due to the pressure drop between the first and the second positions than was originally estimated, such that the temperature variation between the two determination are estimated using the temperature triangle described above.

Embodiments of the above exemplary method for improving resolution of one or more analyte peaks in a chromatographic separation process can include one or more of the following features. In some embodiments, the first and the second positions are the inlet and the outlet, respectively, of the column. In related embodiments the chromatographic separation process is performed using ultra-high performance liquid chromatography, $CO_2$-based chromatography, high temperature liquid chromatography, or chromatography that uses sub-critical or supercritical fluid as the mobile phase.

Additionally, in accordance with embodiments of the present technology a method is disclosed for determining a mobile phase composition for a chromatographic separation process, such that the density and the temperature of the mobile phase remains substantially constant as the mobile phase pressure varies. The method including the steps of (a) providing a first P-T phase diagram having isopycnic curves corresponding to different mobile phase compositions; (b) selecting a range of mobile phase compositions bounded by a first isopycnic curve and a second isopycnic curve, such that, in a pressure interval defined by a first and a second mobile phase pressure, the maximum variation in density of any one of the mobile phase compositions in the range is less than about 0.5 g/L; (c) providing a second P-T phase diagram that includes isenthalpic curves corresponding to a mobile phase composition selected from the range of compositions defined in step (b); and, (c) identifying a mobile phase composition from the second P-T phase diagram, such that the estimated variation in temperature of the mobile phase composition in the pressure interval, estimated using the temperature triangle described above, is less than about 5.0° C., thereby determining the mobile phase composition such that the density and the temperature of the mobile phase remains substantially constant.

In accordance with the embodiments of the present technology an additional method for developing a chromatographic separation process is disclosed. The method includes the steps: (a) selecting a column and a mobile phase composition; (b) providing a pressure-temperature (P-T) phase diagram of the mobile phase, wherein the phase diagram comprises isopycnic curves of the mobile phase and the pressure values range from at least 1000 to at least 6000 psi and the temperature values range from at least 0° C. to at least 200° C.; and (c) operating the chromatographic separation process in a region in the diagram where the mobile phase has a delta density/delta pressure value less than about 80% of the diagram. The mobile phase of the operating chromatographic separation process can be in a supercritical or near supercritical state.

The exemplary methods of the present disclosure provide numerous advantages. For example, the method for estimating temperature variation associated with pressure drop in a mobile phase is highly convenient and requires neither complex calculations nor complex experiments. Because of the ease with which temperature variation may be estimated using the method, the results may be used for many applications, for example, selection of a suitable mobile phase during method development or improvement of resolution of analyte peaks during a chromatographic separation. Further, temperature variation information obtained using the method disclosed can also be readily used for determining mobile phase compositions that can maintain density and temperature at substantially constant levels as mobile phase vary due to pressure drop, which is particularly advantageous in separations carried out using $CO_2$-based chromatography.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 1A is an exemplary diagram showing the effect of thermal heterogeneity in the radial and axial directions on the separation of analytes in liquid chromatography.

DETAILED DESCRIPTION

Provided herein are methods for estimating temperature variations arising from a pressure drop of the mobile phase during a high-efficiency liquid chromatographic separation leading to thermal heterogeneity. Thermal heterogeneity affects the separation of analytes in a mixture because movement of an analyte through a chromatographic column is influenced by temperature of the mobile phase. Thermal heterogeneity may occur both in the axial and radial directions, and may be manifested as a temperature gradient. However, it affects the mobility of the analyte in the axial and radial directions differently. FIG. 1A illustrates how the width of an analyte peak is affected in each case. In the axial direction, temperature gradient acts similarly to a solvent gradient in reverse phase high performance liquid chromatography in that it primarily affects the elution time of the analyte. The width of the analyte peak (10) is not affected significantly. However, radial variation of temperature causes the velocity of the analyte to be different at various locations in the cross-sectional plane of the column. For example, a lower temperature at the center (11) compared to the column wall (12) results in the analyte at the center (11) having a lower velocity relative to that near the wall (12). This leads to distortion and broadening (13, 14) of the analyte peak with accompanying loss of resolution.

Figure 1B:
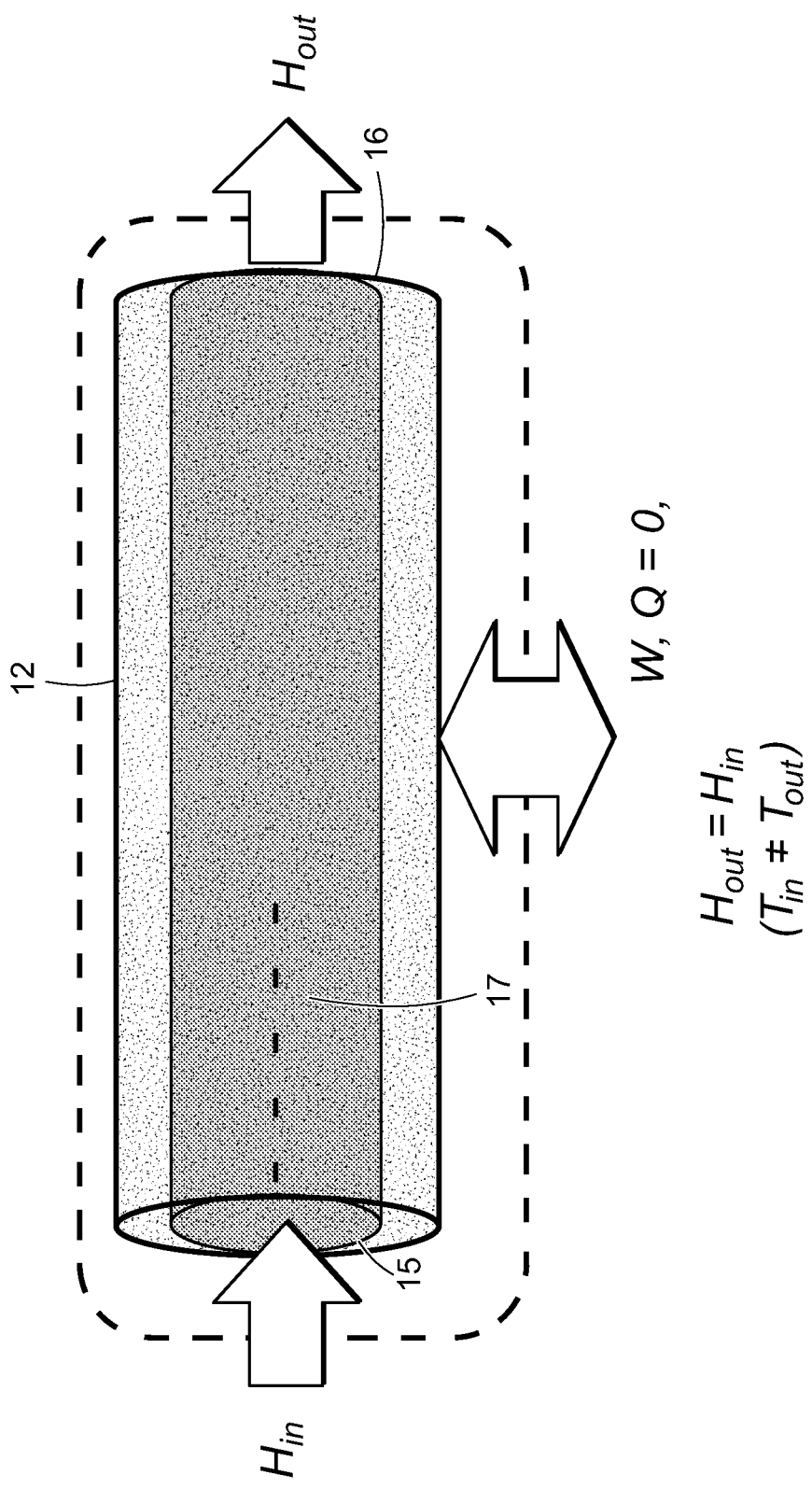
FIG. 1B is an exemplary diagram illustrating energy flow at different boundaries of a chromatography column.

One source of thermal heterogeneity is the pressure drop in the mobile phase that occurs in high efficiency liquid chromatography as the mobile phase is forced through a chromatographic bed of small particle size (e.g., less than about 3 µM; less than about 2 µM, less than about 1 µM, or less than about 0.5 µM) at a high flow rate. Thermal heterogeneity arising from pressure drop can be understood better by considering FIG. 1B which shows energy flow at the different boundaries of a chromatography column, such as the column inlet (15), column outlet (16), and column wall (12). Also shown is the central column axis (17). At the column inlet (15), energy enters with the incoming mobile phase. At the column outlet (16), energy is removed as the mobile phase exits the column. If no energy transfer takes place across the column wall (12), as depicted in FIG. 1B, the mobile phase experiences adiabatic conditions and the enthalpy remains constant. Also, if there is energy transfer at the wall (12), but the energy is not transferred inwards due to poor thermal conductivity, the mobile phase near the column central axis (17) is thermally isolated relative to the column wall, and may be considered to be under an adiabatic condition.

In certain types of chromatography, e.g., ultra-high performance liquid chromatography (UHPLC), the pressure drop leads to a rise in the temperature of the mobile phase due to increased friction between the mobile phase and the particles of the chromatographic bed. Near the column wall (12) the temperature rise in the mobile phase is neutralized due to heat transfer between the column wall (which is maintained at a constant temperature) and the mobile phase. However, around the column central axis (17) the temperature remains high. As the temperature variation affects the analysis of the separation, the ability to understand and in some instances change or modify separation conditions based on temperature variation provides advantages over the current state of the art.

In one embodiment, the present disclosure relates to a method for estimating temperature variation of a mobile phase passing through a column in a chromatographic separation system, the method including providing a pressure-temperature (P-T) phase diagram of the mobile phase, wherein the phase diagram comprises isenthalpic curves of the mobile phase; drawing a triangular figure by connecting a first, second, and a third point on the phase diagram, wherein the first point corresponds to the temperature of the column $T_{first}$ and the mobile phase pressure $P_{first}$ at a first position in the column; the second point corresponds to $T_{first}$ and to the mobile phase pressure $P_{second}$ at a second position in the column; and the third point corresponds to $P_{second}$, and $T_{second}$, wherein $T_{second}$ is the temperature of the mobile phase at the second position, wherein the first and the third points lie on the same isenthalpic curve; and, and estimating the temperature variation by calculating the difference between $T_{first}$ and $T_{second}$. Estimating the temperature variation of a mobile phase passing through a column in a chromatographic separation system is desirable, in part, to understand the extent of heating, or cooling, in the system and to assist in mitigating the heating, or cooling, in the system and its effects.

The mobile phases can include an compressible fluid, such as carbon dioxide, and optionally a modifier, such as methanol. The modifier can be an non-compressible fluid.

The amount of compressible fluid, or fluids, in the mobile phase can be greater than about 10%, 20%, 30%, 40%, 50%, 55%, 60%, 65%, 70%, 75%, 80%, 85%, 90%, 95%, 98%, or 99%. The mobile phase can also be 100% compressible fluid. These values can also be used to define a range, such as between about 70% and about 100%. The amount of non-compressible fluid, or fluids, in the mobile phase can be less than about 90%, 80%, 70%, 60%, 50%, 40%, 30%, 25%, 20%, 15%, 10%, 5%, 2%, or 1%. The mobile phase can also contain 0% non-compressible fluid. These values can also be used to define a range, such as between about 0% and about 30%.

The column can be any column suitable for use in a chromatographic separation process that can experience temperature variation of the mobile phase across the column separation. The chromatographic separation process can be an ultra-high performance liquid chromatography system, a $CO_2$-based chromatography system, a high temperature liquid chromatography system, or a chromatography system that uses sub-critical or supercritical fluid as the mobile phase.

Figure 1C:
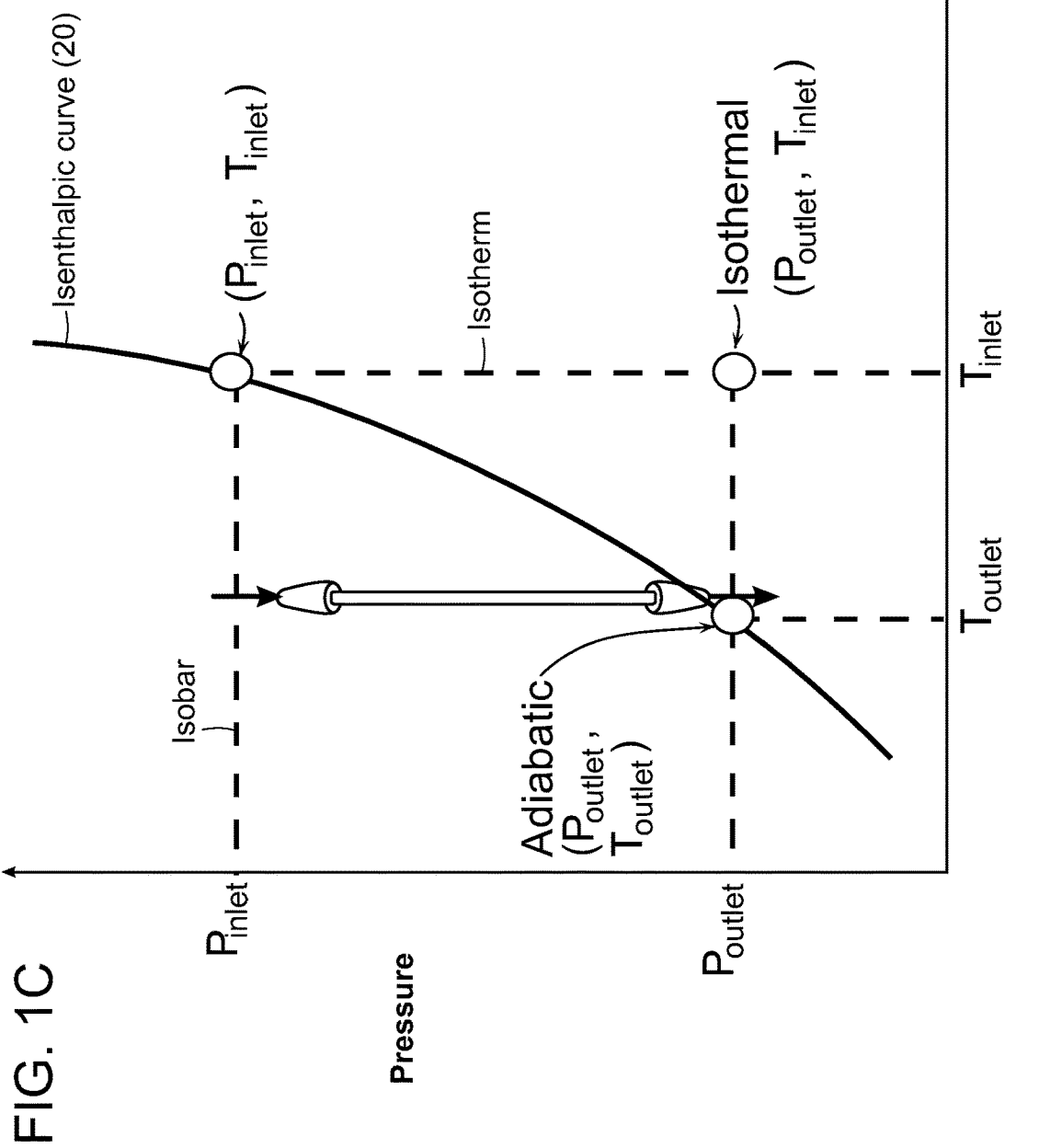
FIG. 1C is an exemplary pressure-temperature phase diagram (P-T diagram) showing an isenthalpic curve for a mobile phase composition. The diagram can be used for estimating temperature difference of the mobile phase during a chromatographic separation process as is passes through a column due to pressure drop in a mobile phase under adiabatic conditions.

Methods for estimating temperature variation in the mobile phase described herein are based on providing thermodynamic plots, specifically pressure versus temperature phase diagrams (P-T diagram) of the mobile phase. The P-T diagram used for this purpose contain constant enthalpy (or iso-enthalpic or isenthalpic) curves, constant density (or isopycnic) curve, or both corresponding to the mobile phase. An isenthalpic curve is one in which all points on the curve represent states of same enthalpy. An isopycnic curve is one in which all points on the curve represent states of same density. Such diagrams are generally available through physical property data banks, e.g., from the NIST (National Institute of Standards and Technology, Gaithersburg, Md.) or the DIPPR (Design Institute for Physical Properties) databanks. The P-T diagram can be used to draw a triangle like figure, the temperature triangle, on the diagram. The temperature triangle can provide a quick estimate of a maximum extent of temperature variation that may occur in the mobile phase during high efficiency chromatography. FIG. 1C is a schematic diagram showing a temperature triangle for a mobile phase under perfectly adiabatic condition. If the inlet pressure and temperature (e.g., as read from the system pressure and oven temperature, respectively), and the outlet pressure are provided (e.g., as read from a back pressure regulator, such as the Automatic Back Pressure Regulator, ABPR in a $CO_2$-based chromatography system), the outlet temperature of the mobile phase can be estimated from the isenthalpic curve corresponding to the mobile phase inlet temperature.

Figure 2:
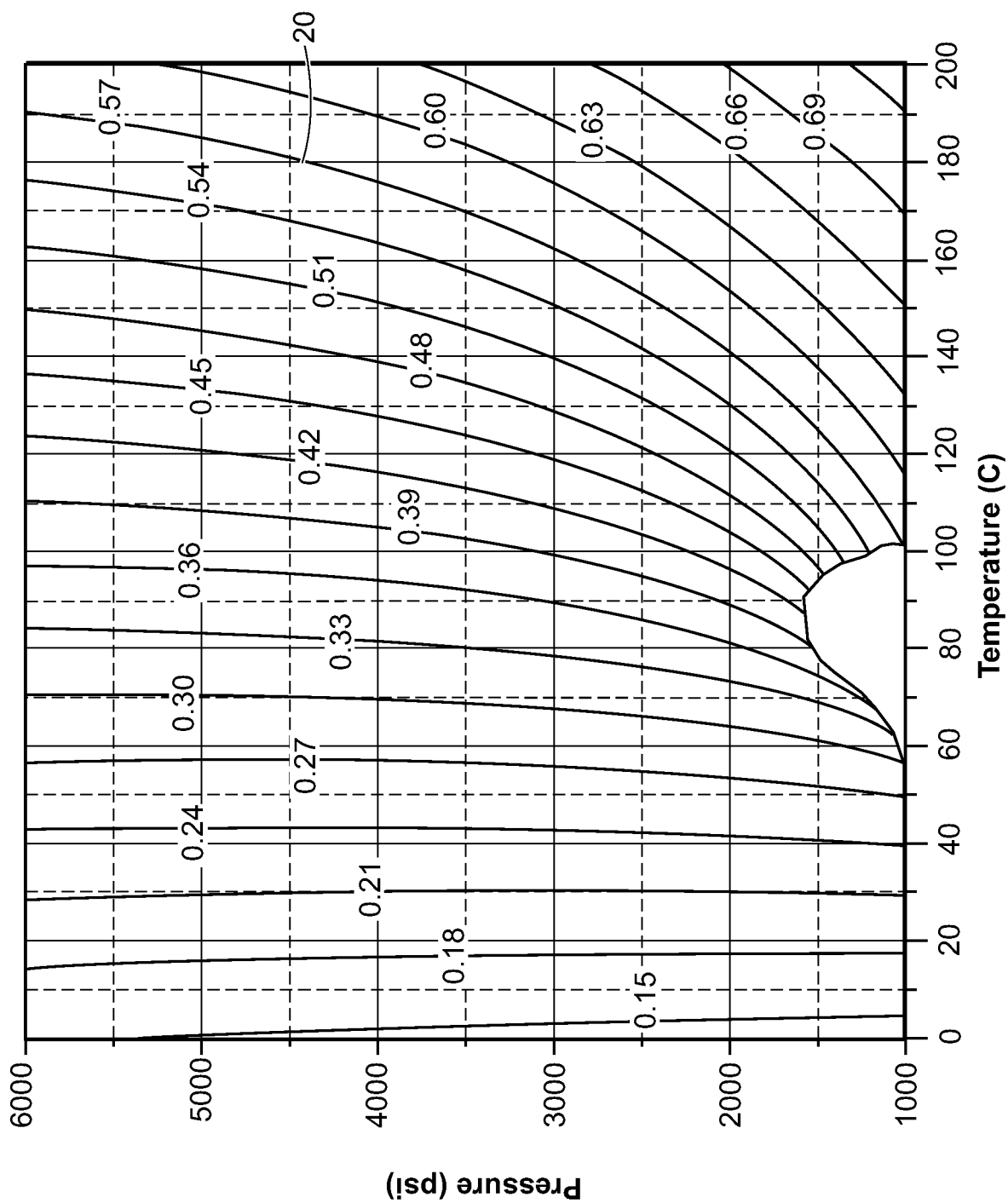
FIG. 2 is an exemplary pressure-temperature phase diagram showing isenthalpic curves for a mobile phase having the composition of 95% $CO_2$ and 5% methanol (95/5 $CO_2$/methanol).
Figure 3:
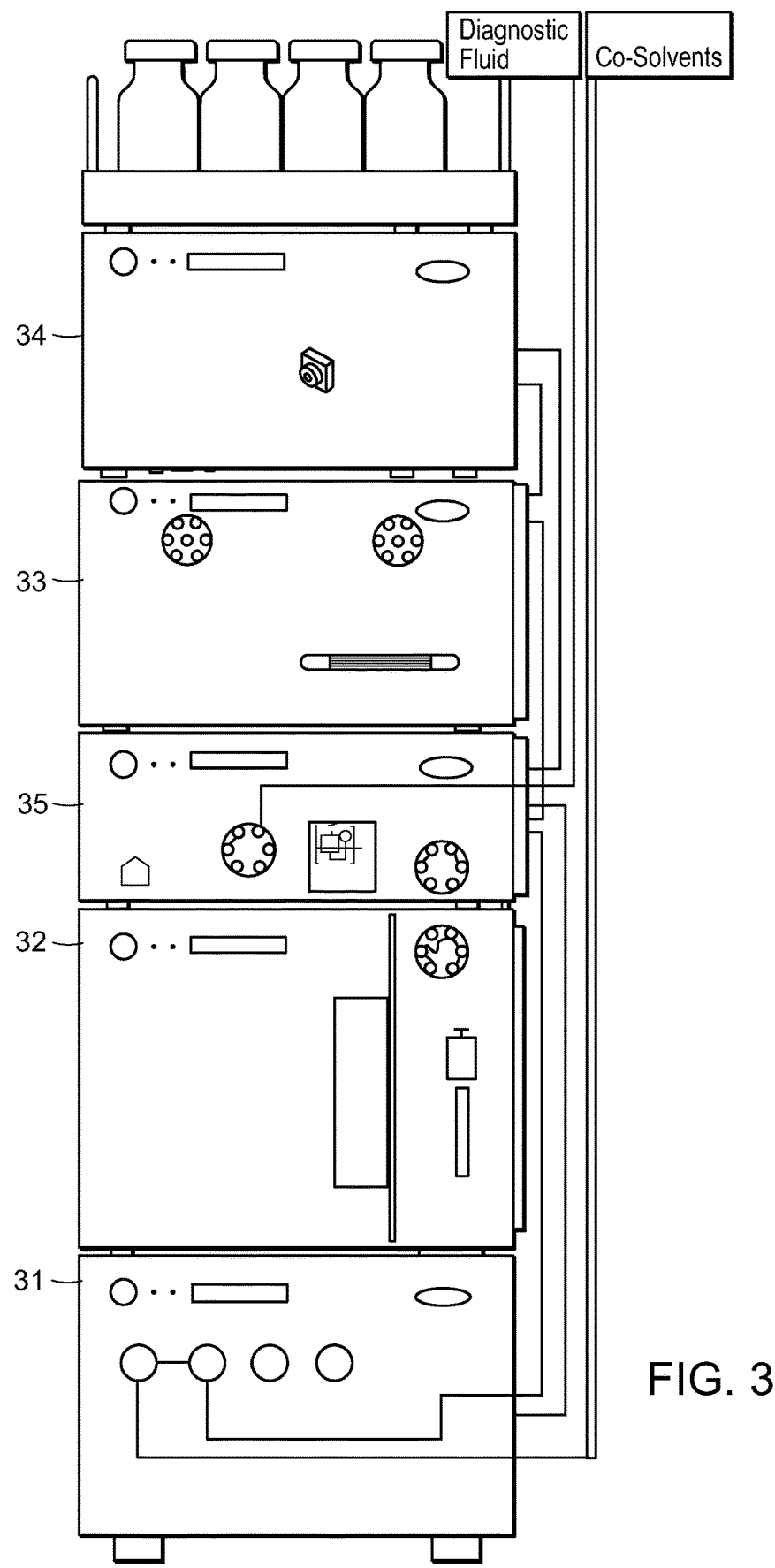
FIG. 3 is an exemplary liquid chromatography system (e.g., a $CO_2$-based chromatography system) depicting different control modules, including a pressurization control module for forming a supercritical or near supercritical conditions of the mobile phase.
Figure 4:
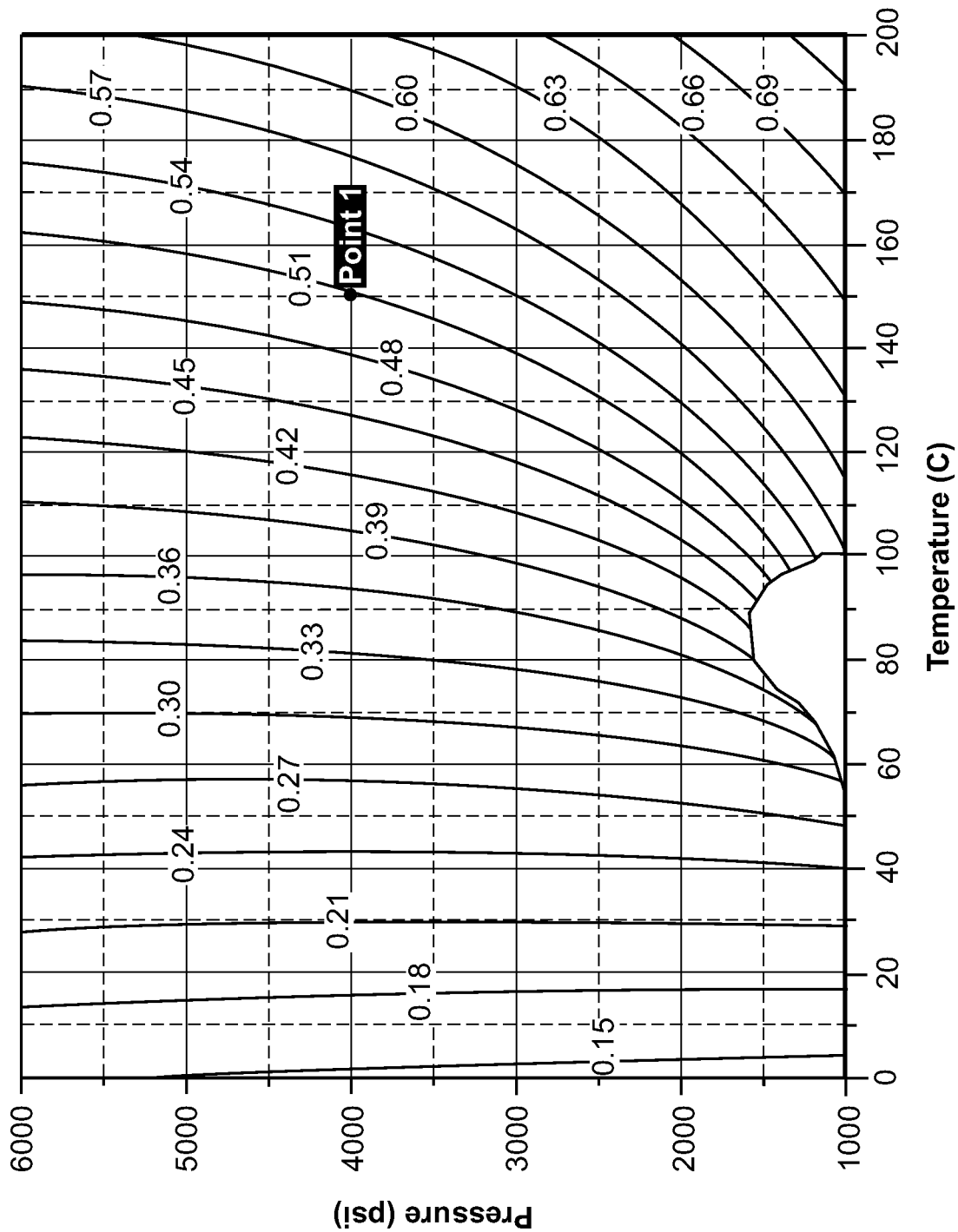
FIG. 4 is an exemplary pressure-temperature phase diagram showing an exemplary "Point 1" corresponding to the mobile phase pressure and temperature of 4000 psi and 151° C., respectively, prior to pressure drop.

FIG. 1C is an illustration of a portion of a P-T diagram of a mobile phase; whereas FIG. 2 shows a P-T diagram of a mobile phase having a particular composition of 95% $CO_2$ and 5% methanol. Lines parallel to x-axis and y-axis are isobars and isotherms, respectively, and the curves are isenthalpic curves of the mobile phase. The construction of an exemplary temperature triangle is described in connection with FIG. 3 (e.g., for an exemplary $CO_2$ based chromatography control system) and in connection with FIGS. 4-8, providing P-T diagrams for a mobile phase of 95% $CO_2$ and 5% methanol (95/05 $CO_2$/methanol mixture). In the first step of constructing the triangle, the system pressure and the column temperature are obtained from the chromatography instrument (FIG. 3) and represented as "Point 1" on the P-T diagram (FIG. 4). For example, in instruments that use the chromatography software Empower (Waters, Milford, Mass.), the system pressure may be obtained from a solvent delivery system module (31), and the column temperature may be obtained from a sample separation module (33) Other modules of the representative $CO_2$-based chromatography control system of FIG. 3 are a sample delivery system (32), a pressurization/supercritical condition control module (35) and a detection system (34).

From the pressure and temperature readings from modules (31) and (33) discussed above, Point 1, as shown in FIG. 4 is identified on a corresponding P-T diagram. Point 1 represents a mobile phase condition before a pressure drop from a sample separation and mobile phase passing through the column. For example, Point 1 can correspond to the system pressure or the mobile phase pressure at column inlet ($P_{inlet}$) and the column temperature, which in this example are 4000 psi and 151° C., respectively. Alternatively, Point 1 can correspond to other mobile phase conditions before another pressure drop in the system. The present disclosure is applicable to systems having pressures of about 100 psi, 200, 300, 400, 500, 600, 700, 800, 900, 1000, 1500, 2000, 2500, 3000, 3500, 4000, 4500, 5000, 5500, 6000, 7000, 8000, 9000 or about 10,000 psi. These values can be used to define a range, such as from about 1000 to about 6000 psi. These values can also be used to define the bounds of the P-T diagrams used to describe the mobile phase properties. Similarly, the present disclosure is applicable to systems having temperatures of about 0° C., 10, 20, 30, 40, 50, 60, 70, 80, 90, 100, 110, 120, 130, 140, 150, 160, 170, 180, 190, or about 200° C. These values can be used to define a range, such as from about 0° C. and about 200° C. These values can also be used to define the bounds of the P-T diagrams used to describe the mobile phase properties.

Figure 5:
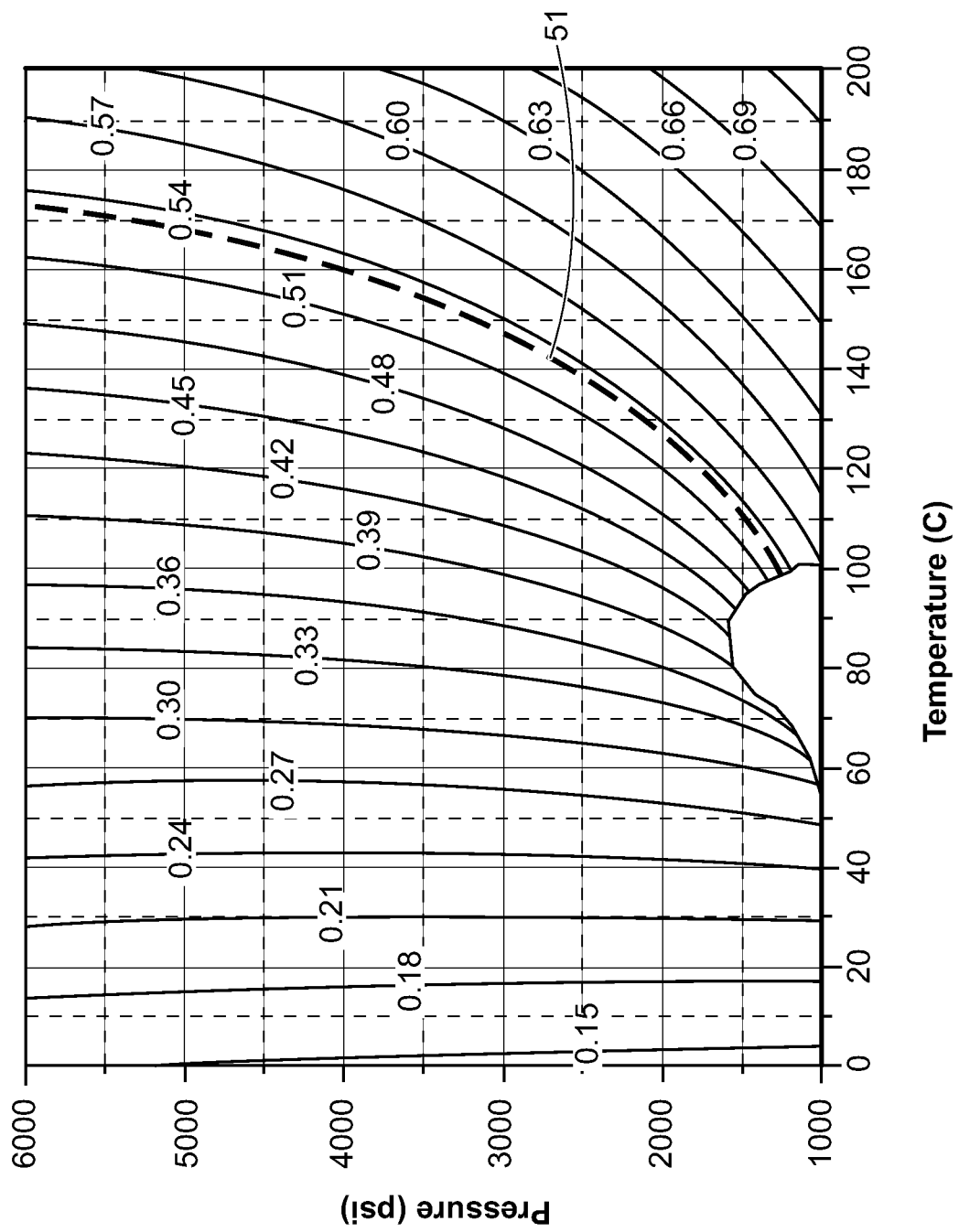
FIG. 5 is an exemplary pressure-temperature phase diagram showing that in case the point representing a particular pressure and temperature coordinate is not located on an isenthalpic curve on the P-T diagram, an interpolated isenthalpic curve can be estimated by the two adjacent isenthalpic curves on the plot. The dashed curve (51) shows one such estimated isenthalpic curve.

The exemplary pressure and temperature chosen, e.g., 4000 psi and 151° C., are simply to aid in the description of constructing the temperature triangle. The construction method described herein is equally applicable for any other temperature. In situations where Point 1 is not located on an isenthalpic curve already present on the plot, an isenthalpic curve can be interpolated between two adjacent isenthalpic curves on the plot. A similar estimation can be made of the isopycnic curves. An example of such a situation is shown in FIG. 5. In FIG. 5, the interpolated curve (51) was generated by interpolation and is shown as a dashed line.

Figure 6:
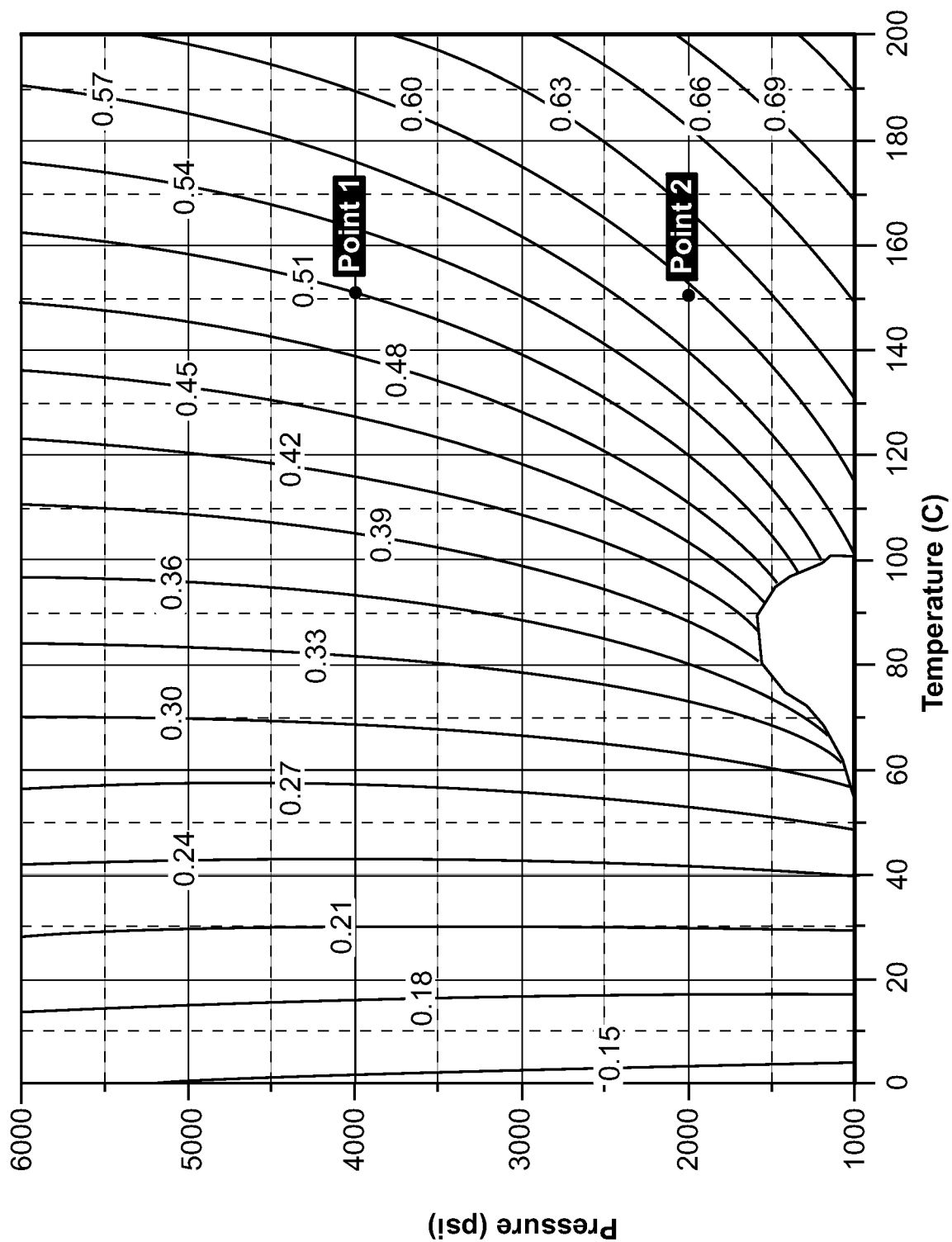
FIG. 6 is an exemplary pressure-temperature phase diagram showing an exemplary "Point 2" corresponding to mobile phase pressure and temperature of 2000 psi and 151° C., respectively, after pressure drop.
Figure 7:
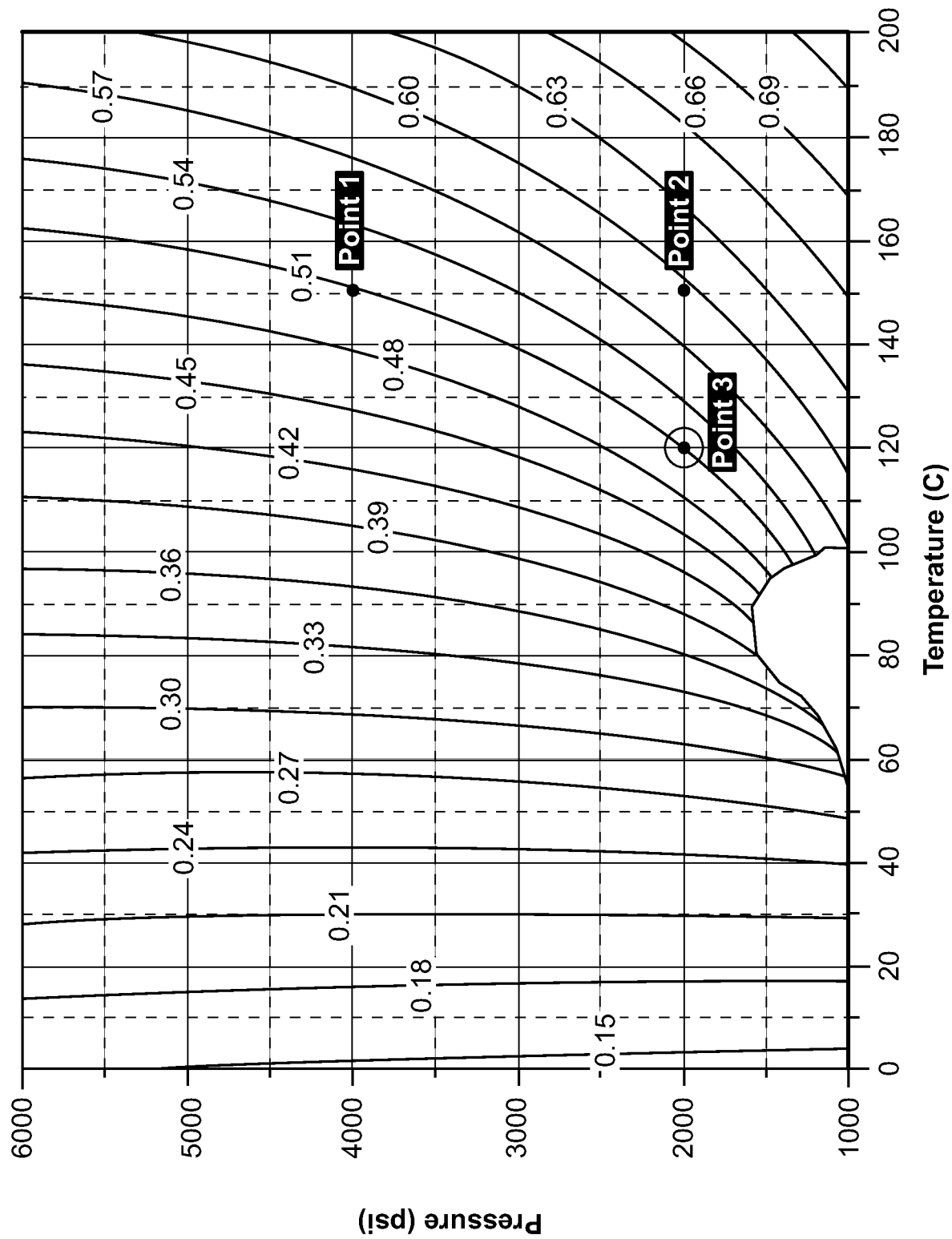
FIG. 7 is an exemplary pressure-temperature phase diagram showing an exemplary "Point 3" in addition to Points 1 and 2. The coordinates of Point 3 correspond to a mobile phase pressure and temperature of 2000 psi and 120° C., respectively. Point 3 lies on the same isenthalpic curve as Point 1.

In the second step to determine the exemplary triangle, the pressure drop at a second point due to the chromatographic separation is utilized in combination with the first point, e.g., the inlet temperature to generate, see FIG. 6. In one embodiment, the mobile phase pressure drop may be obtained from the ABPR, which corresponds to the pressure at column outlet ($P_{outlet}$). In this example, shown in FIG. 6, the pressure is 2000 psi, and the temperature, which remains the same as that for Point 1, is 151° C. See "Point 2" (FIG. 6). In some embodiments, the second position is downstream from the first position. For example, $P_{first}$ and $T_{first}$ can be the pressure and temperature of the mobile phase at the entry point of the column, and $P_{second}$ and $T_{second}$ can be the pressure and temperature of the mobile phase at the exit point of the column.

In the next step a third point is identified on the diagram that lies on the isenthalpic curve passing though "Point 1." A line parallel to the x-axis and passing through Point 2 is drawn. This line is the isobar at the point of pressure drop, for example the ABPR pressure. The isobar meets the isenthalpic curve at a point shown as "Point 3" in FIG. 7. In the current example, the coordinates of Point 3 are 2000 psi and 120° C. A similar exercise and triangle can be generated using isopycnic curves.

Figure 8:
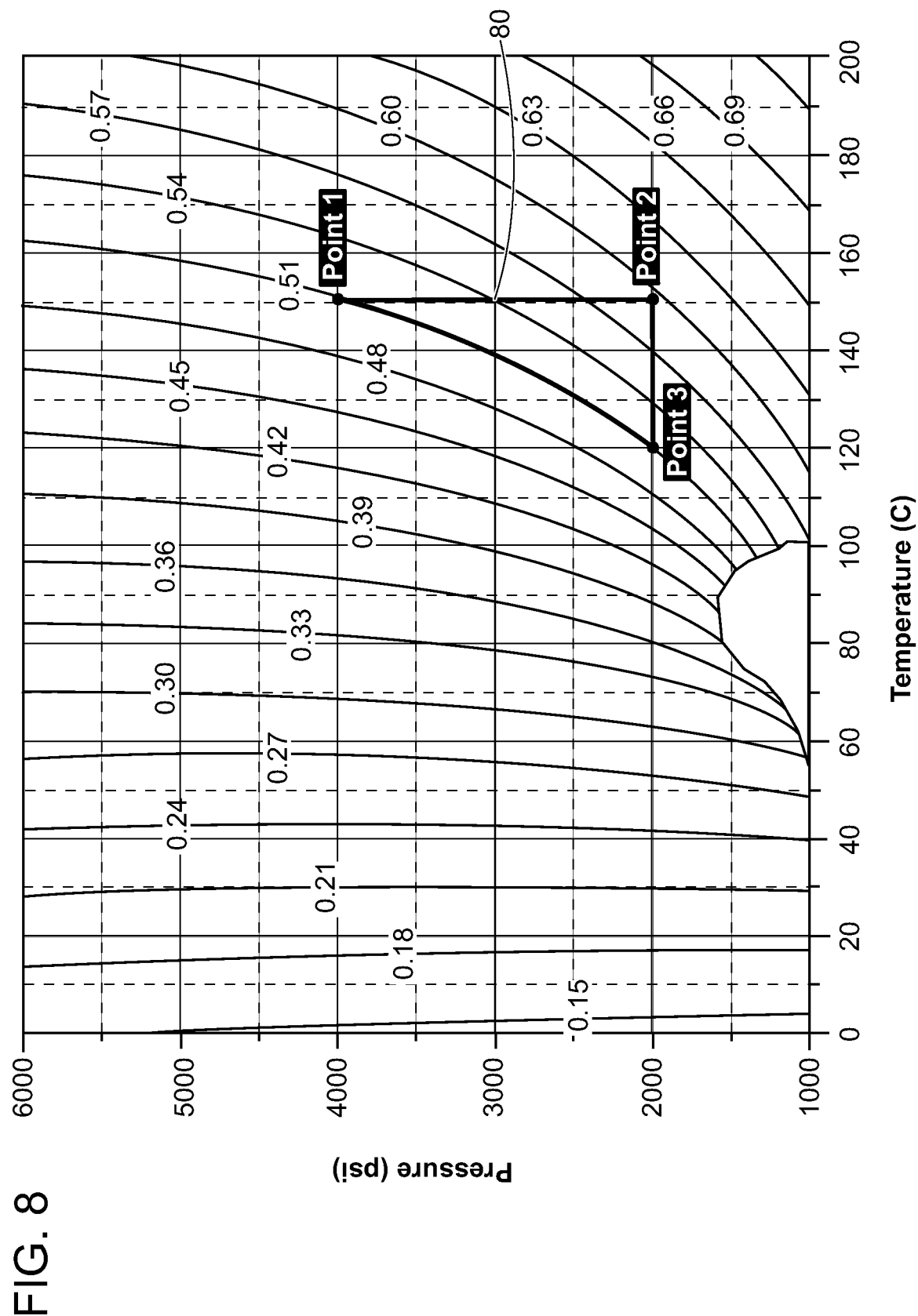
FIG. 8 is an exemplary pressure-temperature phase diagram showing an exemplary triangular figure or "temperature triangle" (80) obtained by joining Points 1 and 2, Points 2 and 3, and Points 1 and 3. Points 1 and 2, and Points 2 and 3 are joined by straight lines. Points 1 and 3 are joined by a curve, i.e., the isenthalpic curve passing through Points 1 and 3.

A temperature triangle can be drawn using these three points. The resultant temperature triangle (80) for the current example is shown in FIG. 8. While Points 1 and 2, and Points 2 and 3 are joined by straight lines, Points 1 and 3 are joined by the isenthalpic curve passing through Points 1 and 3. Although the resulting figure is not strictly a triangle, it is referred to herein as a "temperature triangle."

Figure 9B:
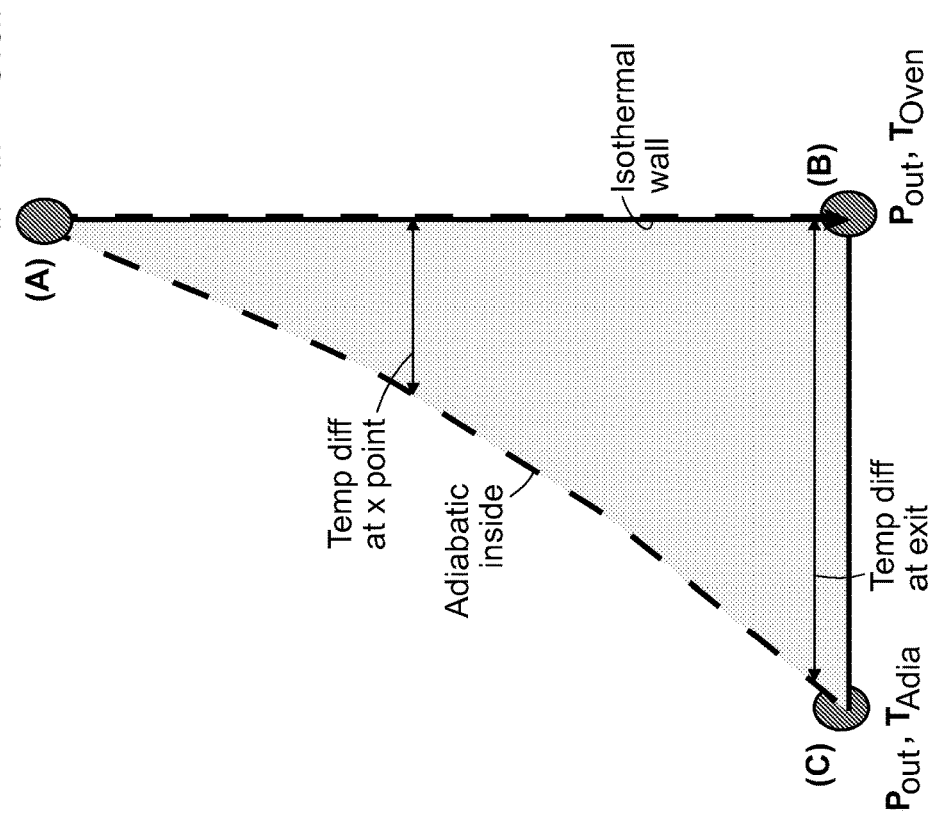
FIG. 9B (right) is an exemplary schematic diagram showing a temperature triangle for quantitation of the maximum expected variation in temperature of the mobile phase in going from the entrance to the exit of the column shown in FIG. 9A.
Figure 9A:
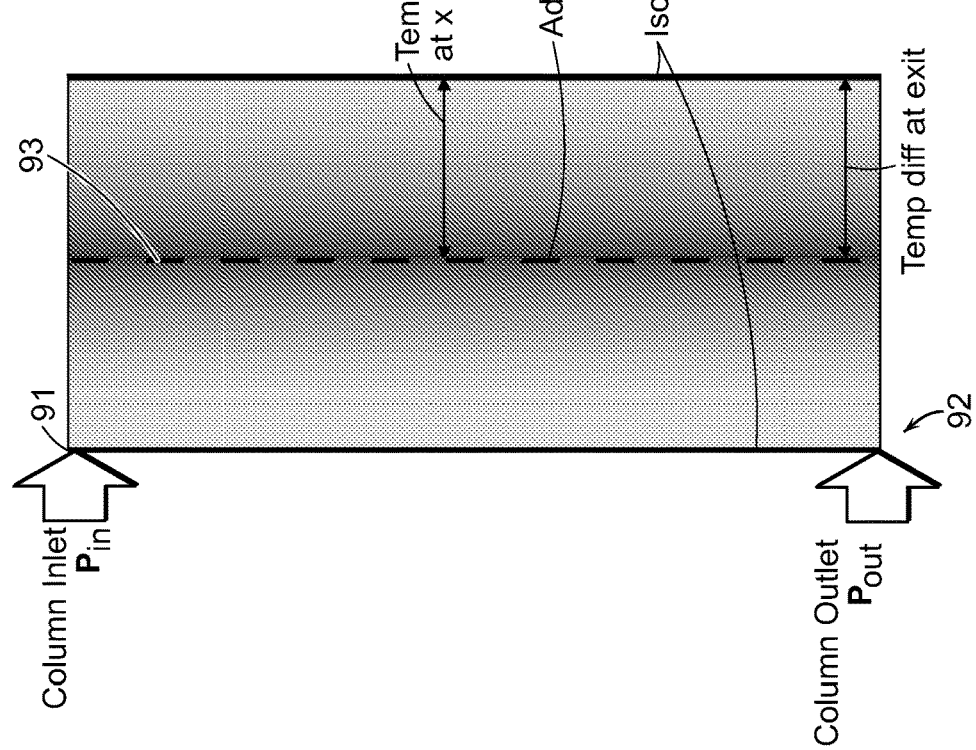
FIG. 9A (left) is an exemplary schematic diagram of a $CO_2$-based chromatography column showing column inlet (91), column outlet (92), and the column central axis (93).

The vertices of the temperature triangle (80), shown both in FIG. 8 and in FIG. 9B, represent different physical locations along the column and corresponding conditions of the mobile phase passing through the column. For example, as shown in FIG. 9B, vertex A (which corresponds to Point 1 of the triangle (80)) represents the pressure and temperature conditions at the column inlet (91). In one embodiment, there can be negligible pressure drop across tubing connecting solvent pump outlets and the column inlet (in some embodiments the inlet is the first position). In addition, the pressure distribution in the radial direction at the column inlet can be assumed to be homogeneous. Further, the temperature of the mobile phase at the column inlet (91) can be assumed to have reached the temperature of the column oven.

Further, in this example vertex B (which corresponds to Point 2 in FIG. 8) represents the column outlet (92) and the condition when the temperature of the mobile phase in the column is unchanged (isothermal condition). In some embodiments, it can be assumed that the pressure drop across tubing connecting the column outlet and the ABPR is negligible; the pressure distribution in the radial direction at the column outlet is homogeneous; and, the heat-transfer between the column and the column oven along the length of the column is effective such that the temperature of the mobile phase is the same (oven temperature) at every location inside the column as the mobile phase passes through the column.

Vertex C (which corresponds to Point 3 in FIG. 8) can represent the column outlet (91) and the pressure and temperature condition when the enthalpy of the mobile phase remains constant (isenthalpic condition). In this example, it can be assumed that the pressure drop across tubing connecting the column outlet and the ABPR is negligible; the pressure distribution in the radial direction at the column outlet is always homogeneous; and the column is thermally insulated from the surroundings so that a perfect adiabatic condition is maintained in the column.

In some embodiments, such as in most situations related to high-efficiency liquid chromatography, the mobile phase conditions at the column wall and around the central axis of the column closely approximate isothermal and adiabatic conditions, respectively.

Figure 10:
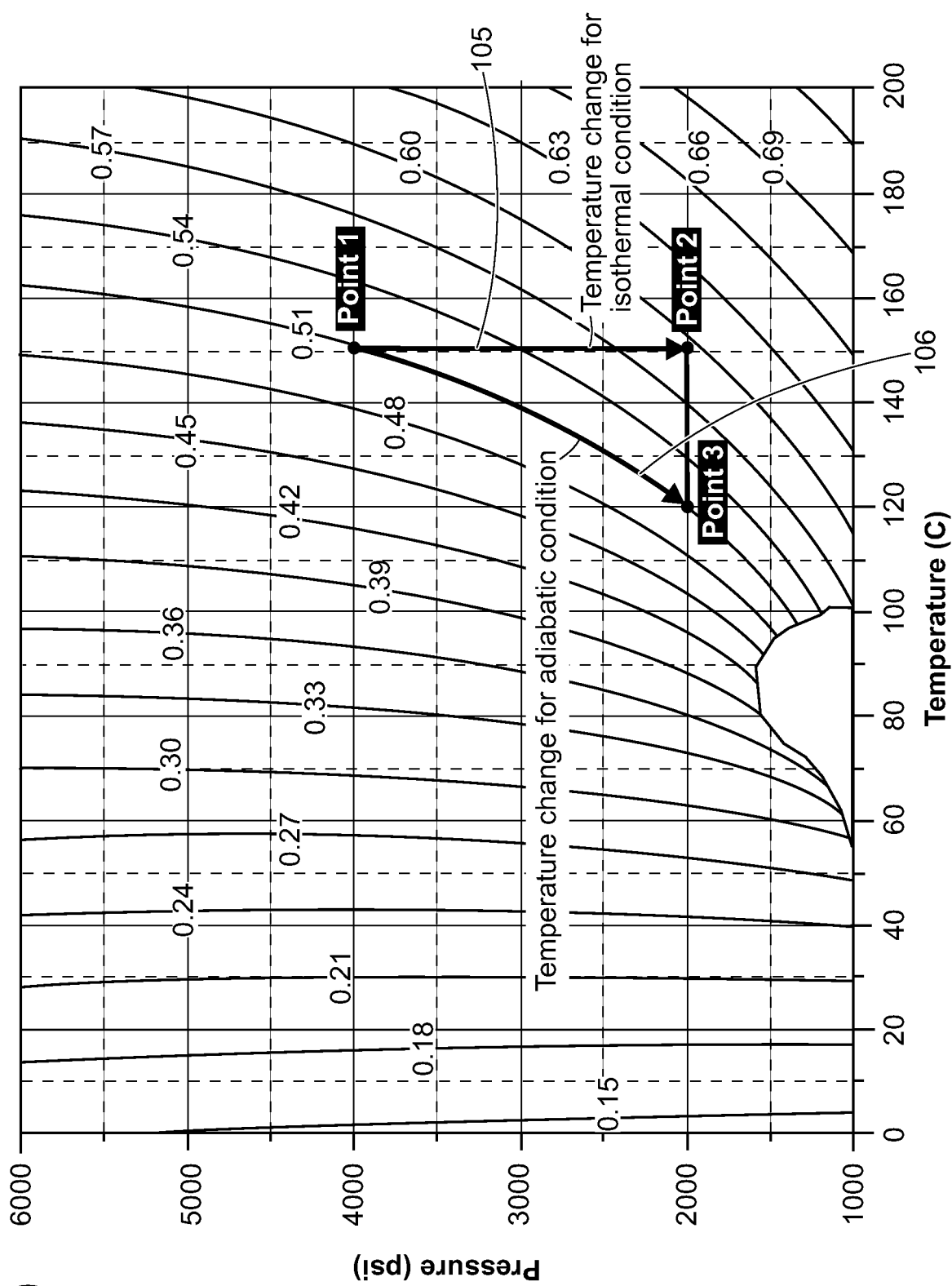
FIG. 10 is an exemplary pressure-temperature phase diagram showing an exemplary temperature triangle that is similar to that shown in FIG. 8. The change for an isothermal condition (105) and the change for an adiabatic condition (106) are shown.
Figure 11:
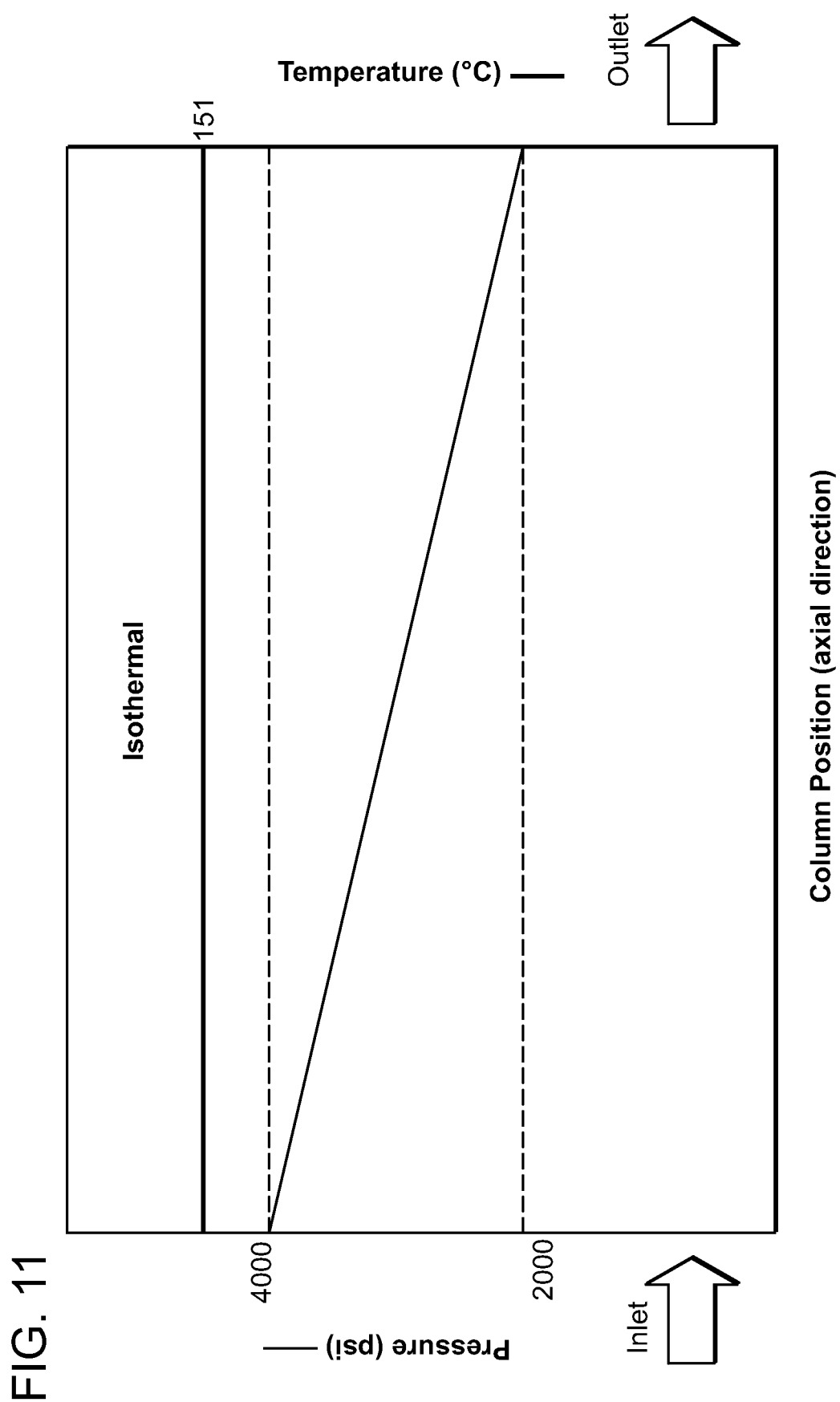
FIG. 11 is an exemplary schematic diagram of the temperature and the pressure profiles represented by the line between Points 1 and 2 of FIG. 8. The profiles are plotted as a function of column position in the axial direction from inlet to outlet. The solid horizontal line at 151° C. exemplifies an isothermal condition.
Figure 12:
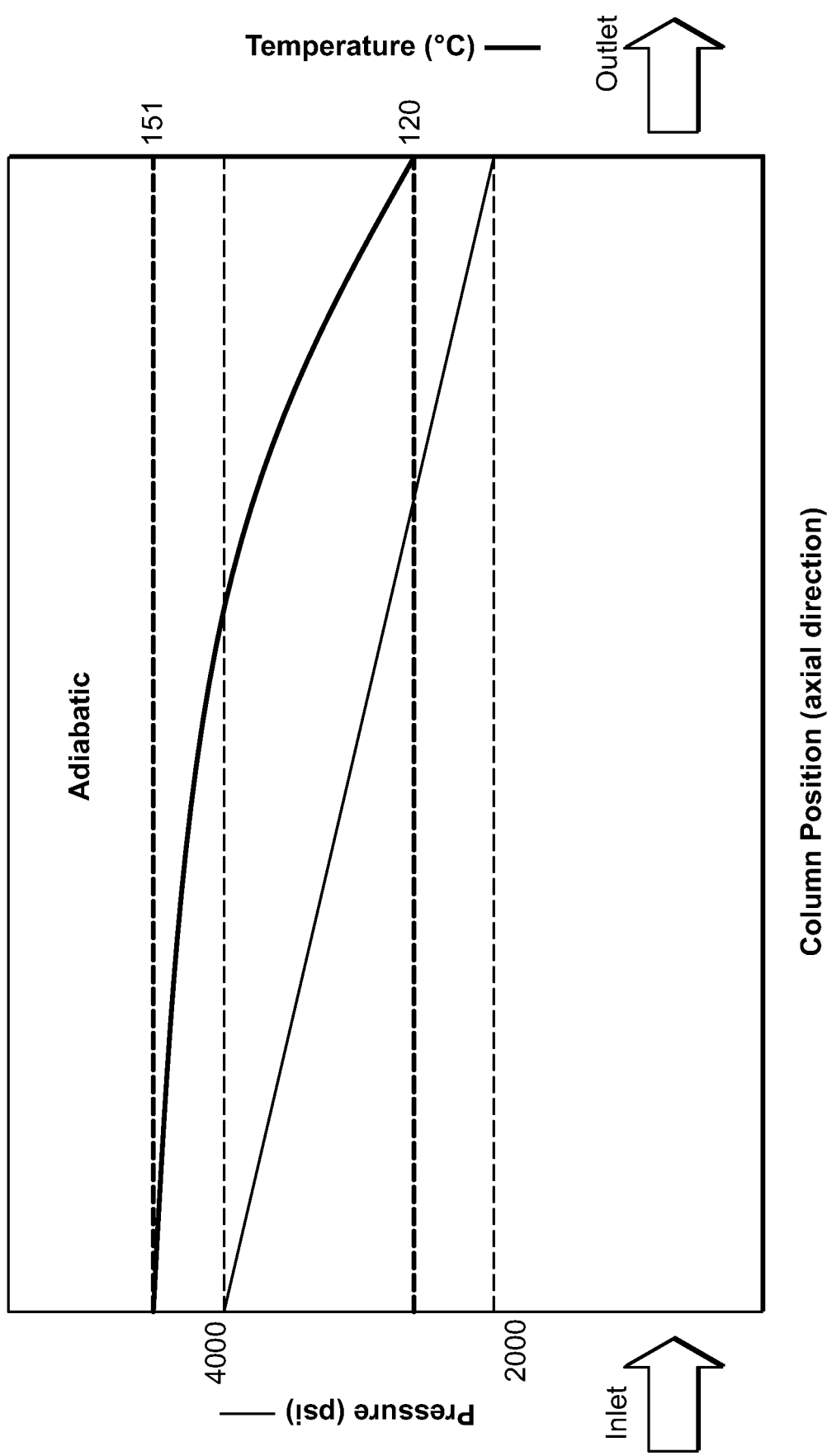
FIG. 12 is an exemplary schematic diagram of the temperature and the pressure profiles represented by the curve joining Points 1 and 3 of FIG. 8. The profiles are plotted as a function of the column position in the axial direction from inlet to outlet. The solid curve connecting the temperature points 151° C. and 120° C. exemplifies an adiabatic condition.

In some embodiments, the experimental conditions with respect to the lines and the curves joining the three vertices of the temperature triangle can include the column temperature being considered homogenous in the radial direction at each cross section of the column. The following conditions can apply to at least the following situations. First, when the entire column is maintained at a perfectly isothermal condition, and second, when the entire column is maintained at a perfectly adiabatic condition. The isothermal condition can be represented by the downward pointing vertical arrow 105 in FIG. 10 that joins Points 1 and 2. The curve joining Points 1 and 3 (curved arrow 110 in FIG. 10) represents the temperature and pressure profile of the mobile phase as it passes through the column when the condition is adiabatic. Points 1 and 3 represent temperatures and pressures of the mobile phase, at the inlet and outlet, respectively. Schematic diagrams of the temperature and the pressure profiles represented by the line joining Points 1 and 2 (isothermal condition), and the curve joining Points 1 and 3 (adiabatic condition), plotted as functions of the column position in axial direction are also shown in FIGS. 11 and 12.

Figure 13:
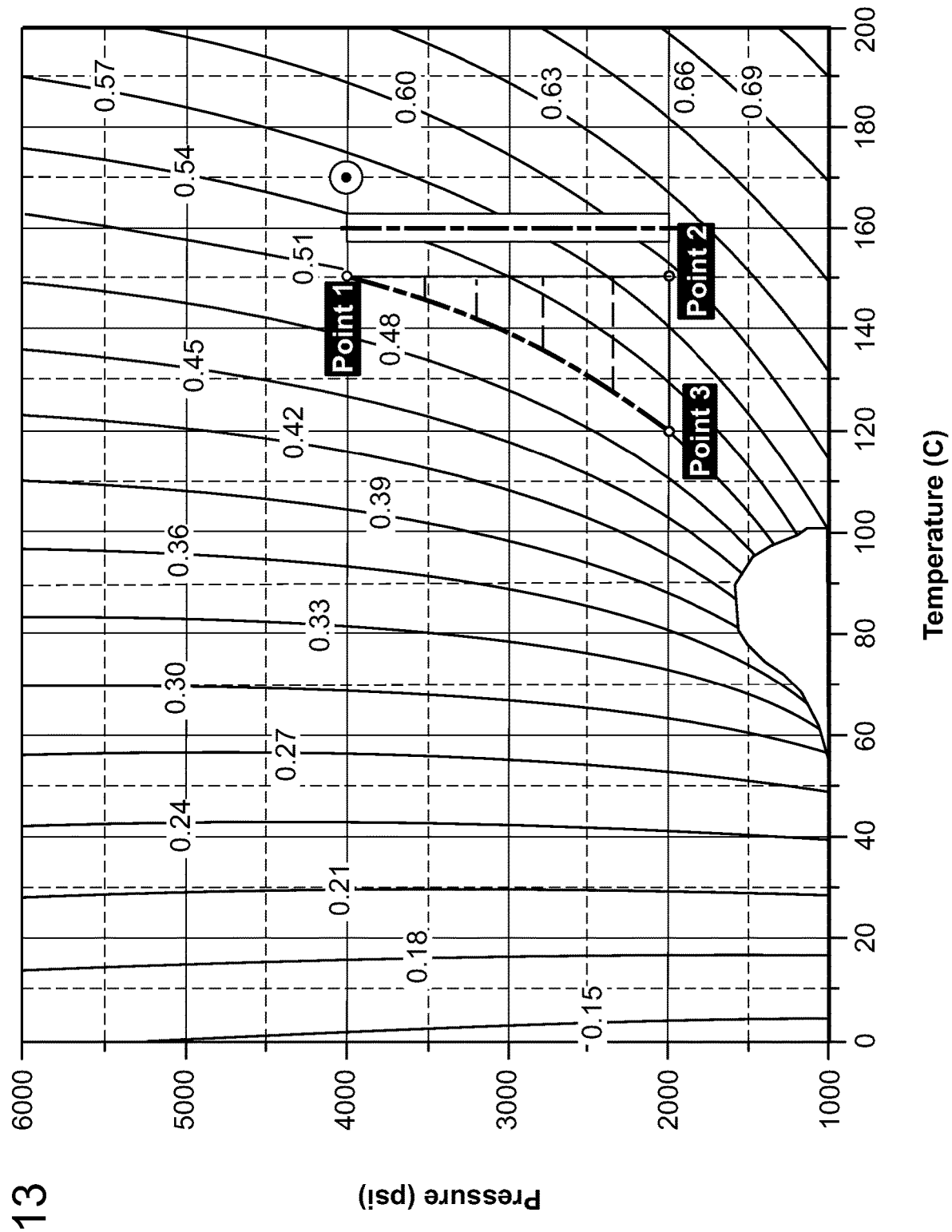
FIG. 13 is an exemplary pressure-temperature phase diagram similar to that shown in FIG. 8 wherein the dashed horizontal lines within the temperature triangle represent temperature differences between the column center and the column wall at various points along the length of the column.

In other embodiments, the experimental conditions with respect to the lines and the curves joining the three vertices of the temperature triangle can include the column temperature being considered non-homogenous in the radial direction at each cross section of the column. This condition can be reflective of real operating conditions, in which the column is kept in a thermostatic environment, e.g., a column oven (or open to room temperature) such that the column wall is exposed to a constant temperature environment, and there is heat transfer between the wall and the mobile phase close to the wall which neutralizes the temperature variation in the mobile phase near the wall. Because of inefficient thermal conductivity of the mobile phase and the chromatographic bed, however, the temperature change due to pressure drop along the column axis (e.g., 93 in FIG. 1B) may not be able to be neutralized. The mobile phase in the interior of the column, along the axis (93) can experience conditions approximating adiabatic conditions. Under perfectly adiabatic conditions the enthalpy inside a chromatographic column remains constant. Therefore, the mobile phase temperature at the column axis ($T_{outlet}$), at the point of pressure drop ($P_{outlet}$) can be determined by the point of intersection (Point 3) of the isenthalpic curve corresponding to the starting temperature and pressure (Point 1) and the isobar for the final pressure. The mobile phase temperature, at the column wall ($T_{inlet}$) at the point of pressure drop ($P_{outlet}$) can be determined from the set oven temperature. Thus, the maximum temperature variation due to pressure drop can be estimated by the temperature difference between $T_{inlet}$ and $T_{outlet}$. See FIGS. 10 and 13. Further, the maximum temperature variation for different pressure drops by can be estimated by drawing lines parallel to the X-axis within the temperature triangle as shown in FIG. 13.

The method provided herein may be used for many purposes. In one embodiment, the present disclosure is related to a method of developing a chromatographic separation process, the method including selecting a column and a first mobile phase composition; estimating temperature variation in the first mobile phase composition between pressures $P_{inlet}$ and $P_{outlet}$ as described herein, wherein $P_{inlet}$ and $P_{outlet}$, respectively, are the pressures of the mobile phase at the entry point and at the exit point of the column; and determining a second mobile phase composition for the process, wherein the estimated temperature variation in the second mobile phase composition between $P_{inlet}$ and $P_{outlet}$ is different from that in the first mobile phase composition.

Figure 14:
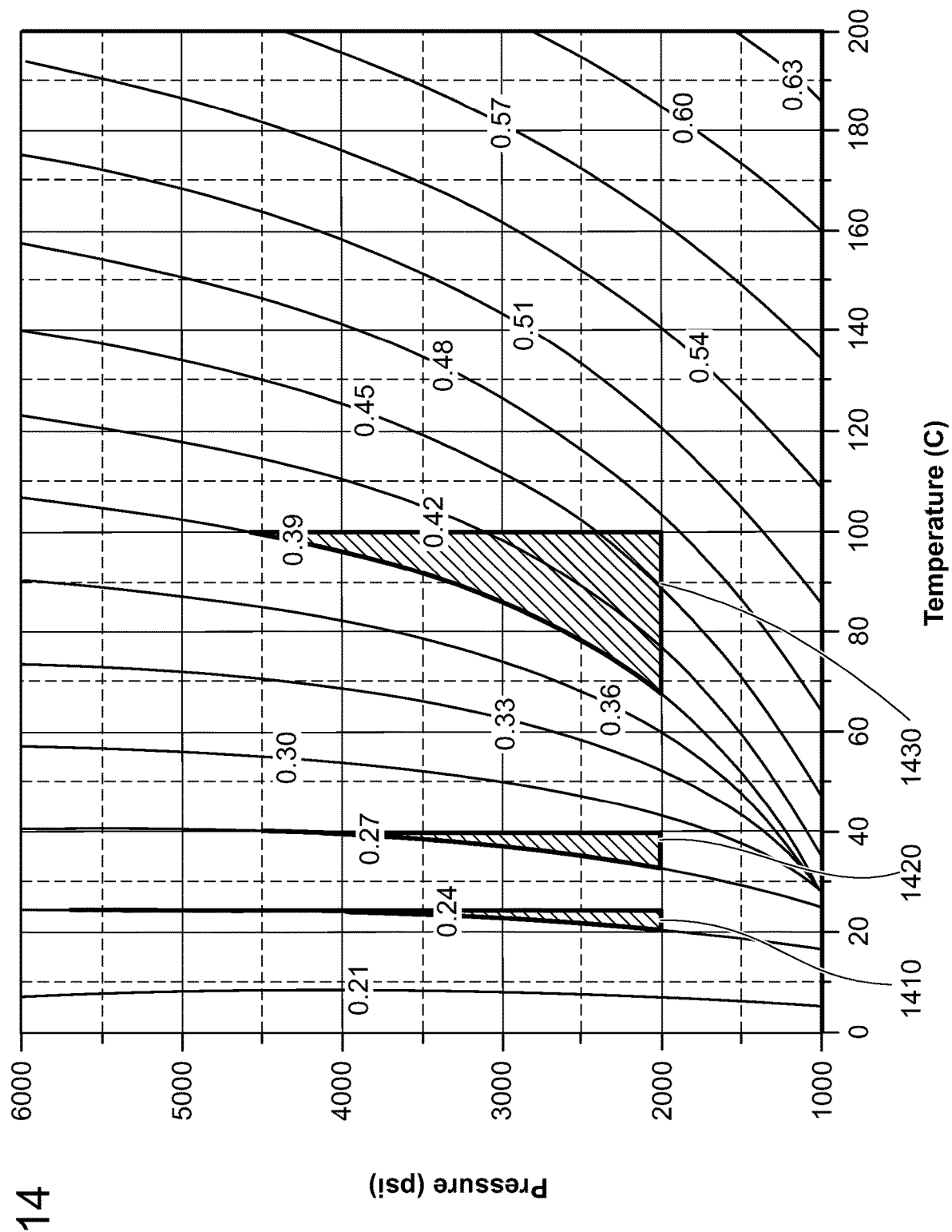
FIG. 14 is an exemplary pressure-temperature phase diagram showing different estimated maximum temperature variations in the mobile phase in a $CO_2$-based chromatography system corresponding to different inlet temperatures wherein the inlet and the outlet pressures remain constant (e.g., 1410, 1420 and 1430). In each case the outlet temperature is determined by a different isenthalpic curve.

For example, as shown in FIG. 14, the method can be used to generate temperature triangles for a number of different inlet temperatures of a mobile phase. These different inlet temperatures can be evaluated for the maximum temperature variation that would result from selecting any one of the inlet temperatures (e.g., in one embodiment as shown the inlet and the outlet pressure remain constant) in order to then select an inlet temperature that result in a smaller temperature variation. In some instances, a smaller temperature variation can be an optimal or optimized conditions for a given $CO_2$ based chromatography separation. The temperature variation can be differ (e.g., be smaller or larger) by at least 5%, 10%, 15%, 20%, 25%, 30%, 35%, 40%, 45%, 50%, 55%, 60%, 65%, 70%, 75%, 80%, 85% or 90%. These values can also be used to define a range, such as about 10% to about 50%. For example, the temperature triangles (1410), (1420), and (1430) show that for a given pressure drop, selecting an inlet temperature corresponding to triangle (1410) would result in the least temperature variation, followed by selecting that corresponding to the triangle (1420). The temperature variation due to pressure drop would be the highest for the inlet temperature corresponding to the triangle (1430).

The method can also be used for improving the resolution of analyte peaks in liquid chromatography. For example, temperature variation in a first mobile phase composition arising from pressure drop can first be estimated using the temperature triangle described above. Next, temperature variation for the same pressure drop can be estimated for other mobile phase compositions, and a composition can be selected that has a lower estimated temperature variation. Use of the mobile phase having a lower estimated temperature variation can reduce the width of an analyte peak compared to the width obtained with the use of the first mobile phase composition at the beginning of the process.

In another embodiment, the present disclosure relates to a method for improving resolution of one or more analyte peaks in a chromatographic separation process, the method including estimating the temperature variation in a first mobile phase as described herein; and, obtaining a reduction in width of at least one of the one or more analyte peaks by substituting the first mobile phase with a second mobile phase having a different composition, wherein the estimated temperature variation in the second mobile phase as described herein is different compared to that estimated for the first mobile phase. The temperature variation can be differ (e.g., be smaller or larger) by at least 5%, 10%, 15%, 20%, 25%, 30%, 35%, 40%, 45%, 50%, 55%, 60%, 65%, 70%, 75%, 80%, 85% or 90%. These values can also be used to define a range, such as about 10% to about 50%. In particular, the estimated temperature variation in the second mobile phase is smaller than that estimated for the first mobile phase.

Figure 15:
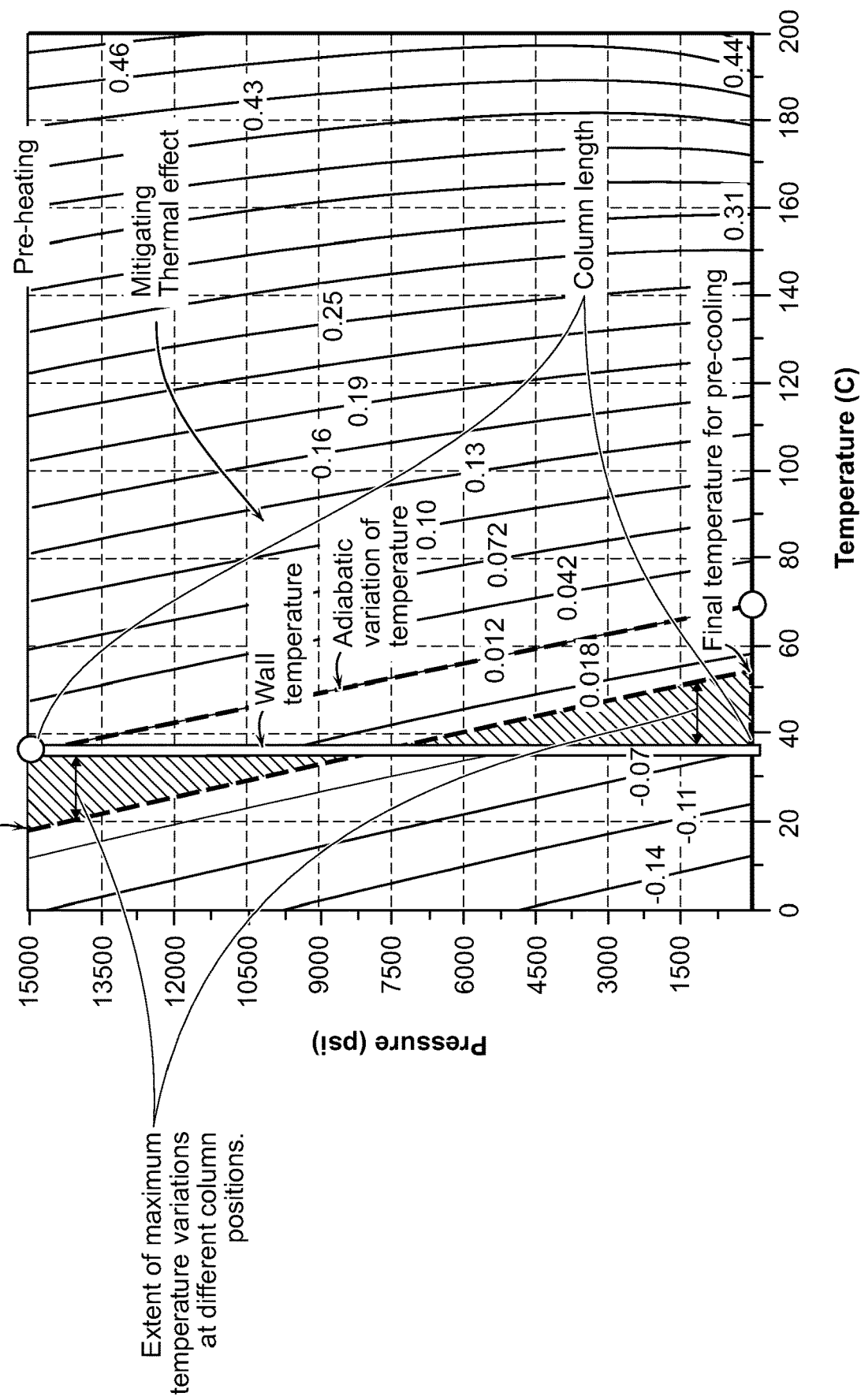
FIG. 15 is an exemplary pressure-temperature phase diagram showing the effects of pre-cooling of the mobile phase to mitigate the effect of temperature rise due to the pressure drop.

The method of the present disclosure can further be used for designing thermal mitigators for liquid chromatography. These mitigators can include pre-cooling/pre-heating the mobile phase before entry into the column, cooling/heating the column at different points along the column length, or combinations thereof. In particular, the cooling/heating of the column can be a performed as a gradient along the length of the column. The gradient can be matched to offset or mitigate the temperature variation in the column. For example, in an UHPLC separation for which the temperature difference due to pressure drop is estimated to be about 40° C., the mobile phase may be pre-cooled by approximately 20° C. to nullify the temperature effect of the pressure drop. The pre-cooling/pre-heating of the mobile phase can be about 10%, 15%, 20%, 25%, 30%, 35%, 40%, 45%, 50%, 55%, 60%, 65%, 70%, 75%, 80%, 85%, 90%, 95% or 100% of the estimated temperature difference. These values can also be used to define a range, such as about 10% to about 50%. FIG. 15 shows a pressure-temperature diagram illustrating the pre-cooling effect. In this manner, the band distortion or broadening due to thermal effect could be reduced, minimized or avoided.

Figure 16:
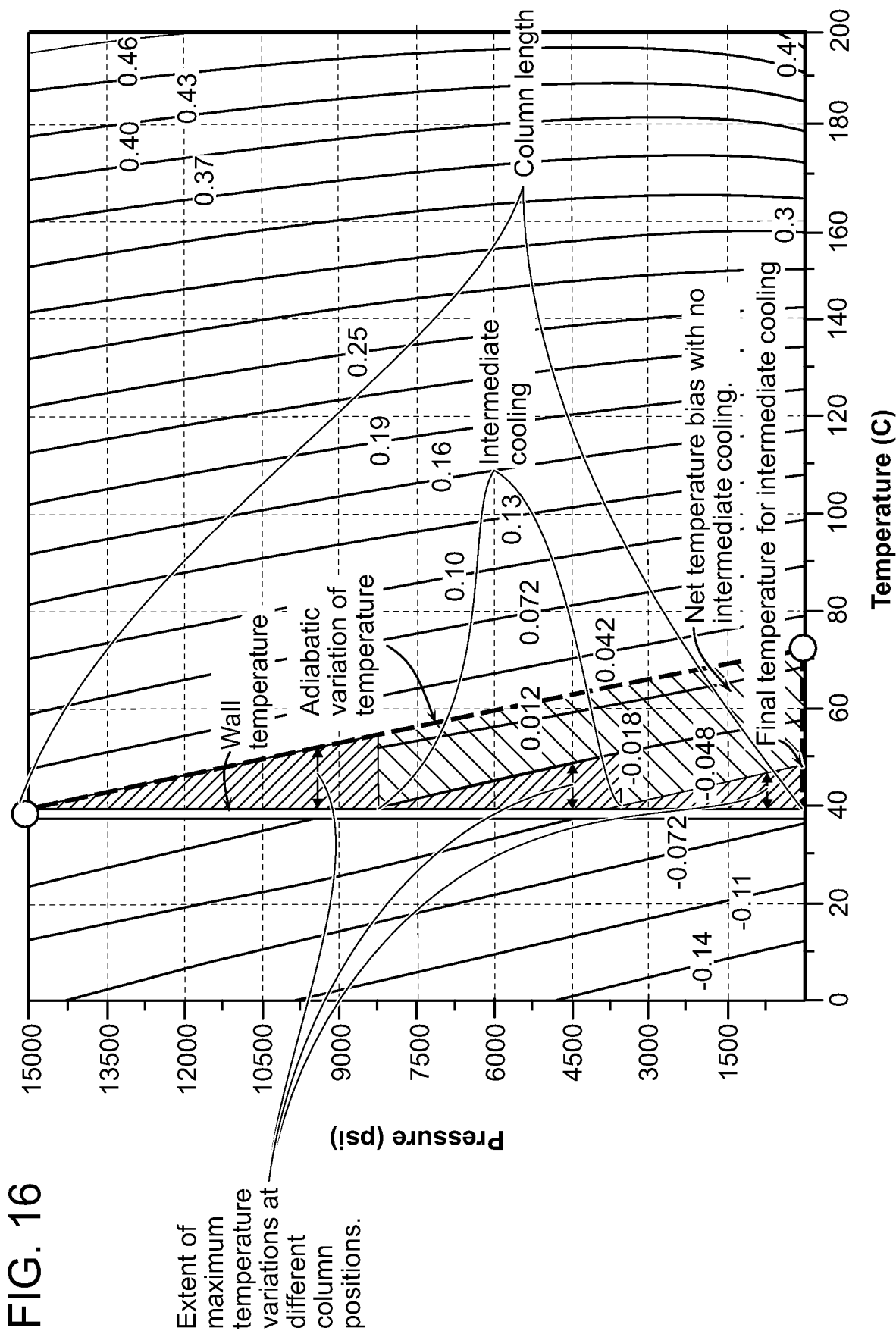
FIG. 16 is an exemplary pressure-temperature phase diagram showing the effects of cooling of the column different positions along the length of the column to mitigate the effect of temperature rise due to the pressure drop.
Figure 17:
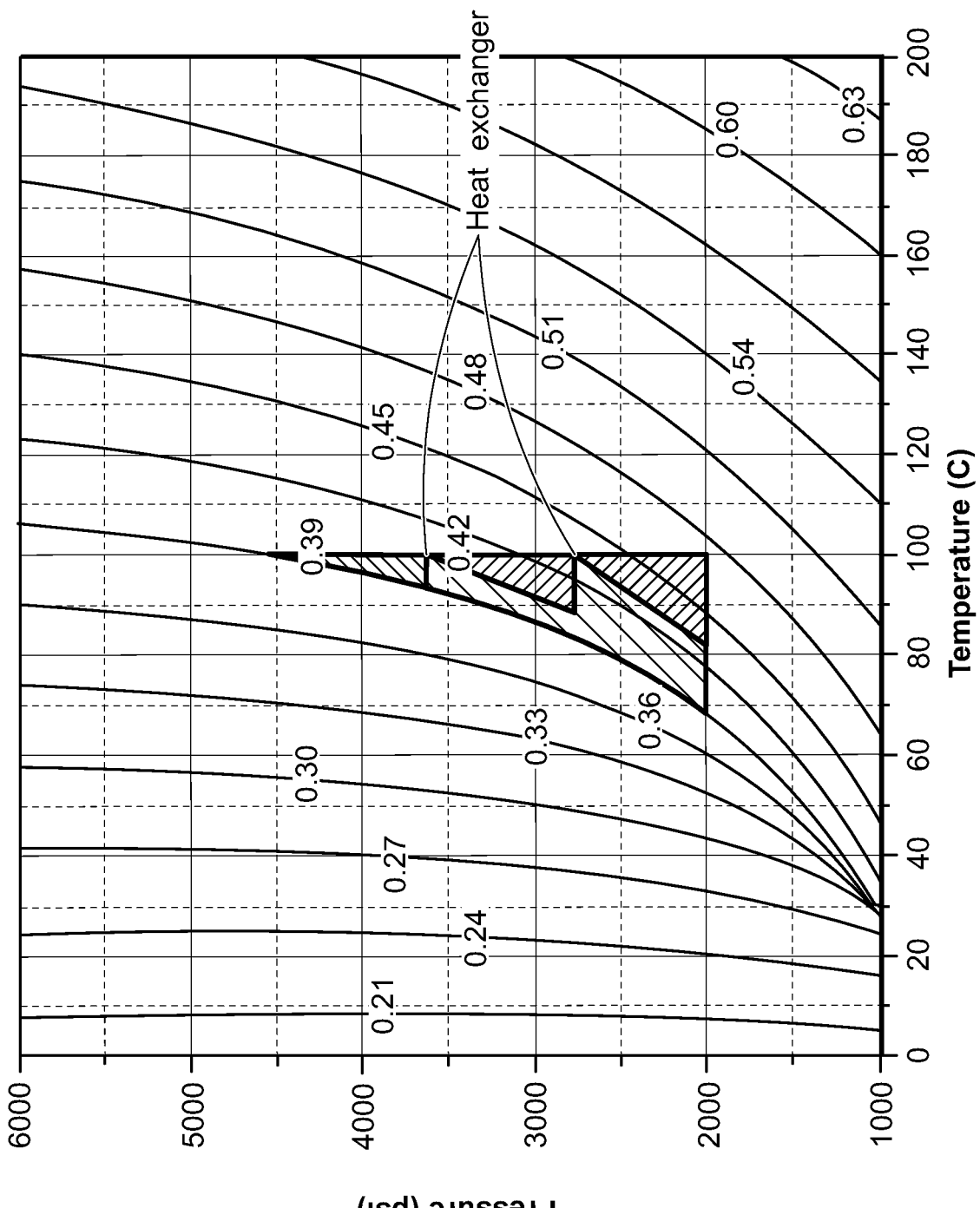
FIG. 17 is an exemplary pressure-temperature phase diagram showing the use of heat exchangers for raising the temperature at different positions in the column to mitigate the effect of temperature variation in the mobile phase.
Figure 18:
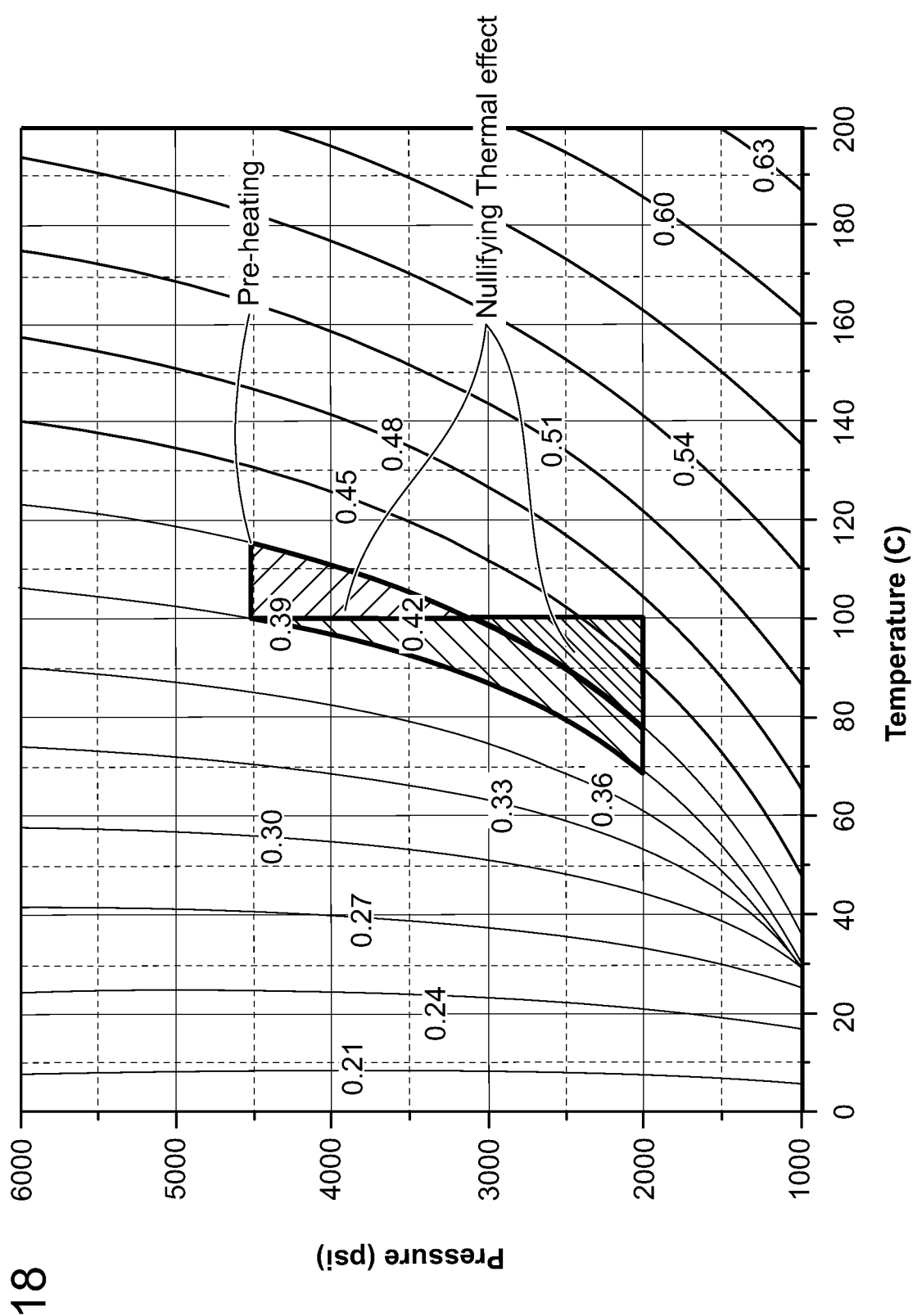
FIG. 18 is an exemplary pressure-temperature phase diagram showing the effects of pre-heated mobile phase to mitigate the extent of temperature variation in the mobile phase.

FIGS. 16-18 show a pressure-temperature diagrams illustrating the intermediate cooling of the column at different positions along the length of the chromatography column. In some embodiments, intermediate cooling may not eliminate the temperature change completely, but it can greatly reduce the temperature change. FIG. 16 shows that the more intermediate cooling steps used, the lesser the magnitude of net temperature difference. FIG. 17 shows the use of heat exchangers for raising the temperature at different positions in the column to mitigate the effect of temperature variation in the mobile phase. FIG. 18 shows the effects of pre-heated mobile phase to mitigate the extent of temperature variation in the mobile phase.

In another embodiment, the present disclosure relates to a method for improving resolution of one or more analyte peaks in a chromatographic separation process, the method including providing a column and a mobile phase; estimating the temperature variation in the mobile phase between a first position and a second position in the column as described herein; and, pre-cooling or pre-heating the mobile phase by a temperature equal to or less than the estimated temperature variation.

In another embodiment, the present disclosure relates to a method for improving resolution of one or more analyte peaks in a chromatographic separation process, the method including providing a column and a mobile phase; estimating the temperature variation in a first mobile phase between a first position and a second position in the column as described herein; and cooling or heating the column at one or more positions along the length of the column during the separation process, wherein the cooling or heating results in a smaller estimated temperature variation in the mobile phase between the first and the second positions as described herein than that first estimated. The first position can be the column inlet and the second position can be the column outlet. The cooling or heating of the column at one or more positions along the length of the column can result in a gradient that changes from the column inlet to the column outlet.

Figure 19:
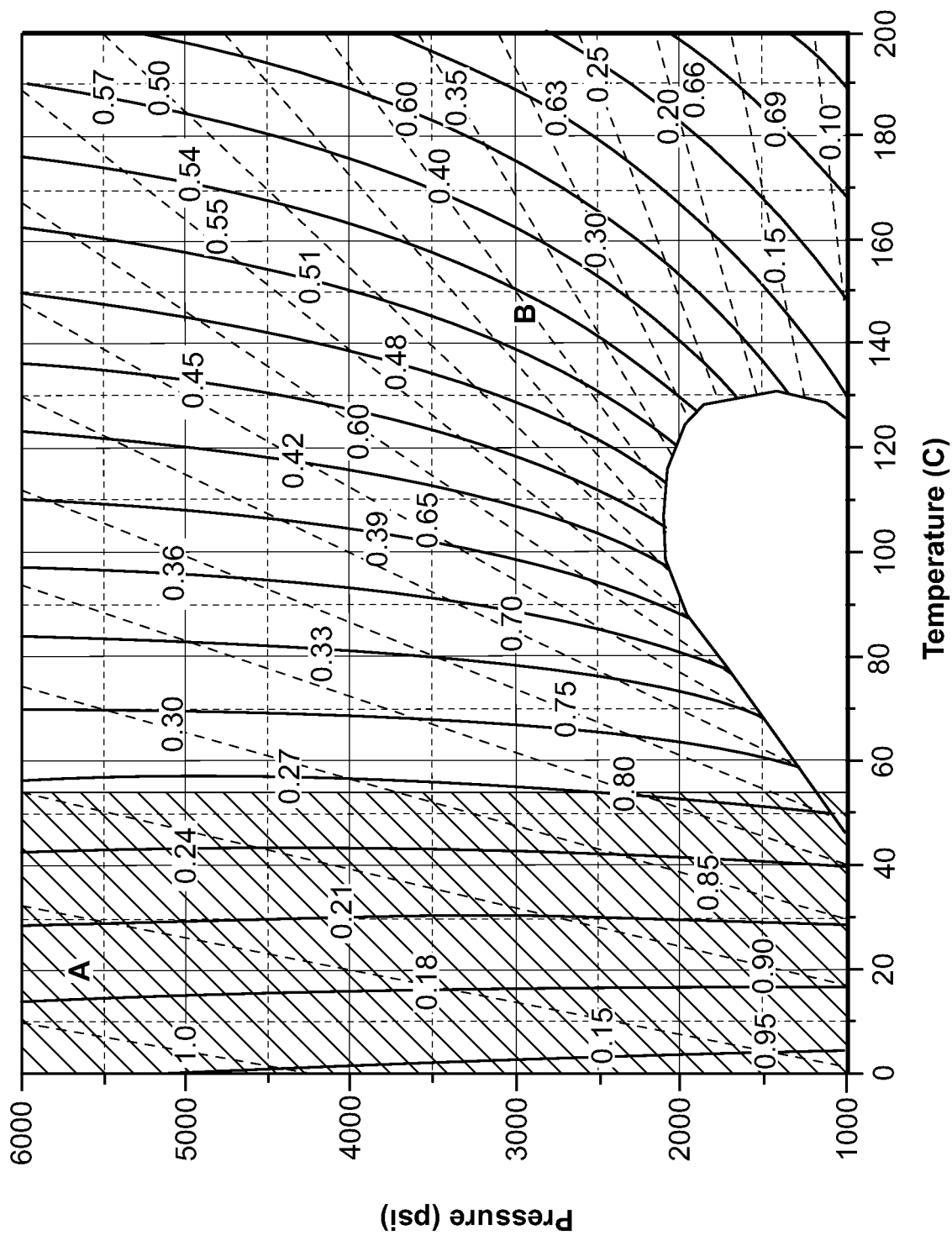
FIG. 19 is an exemplary pressure-temperature phase diagram showing isenthalpic curves for a mobile phase having the composition of 80% $CO_2$ and 20% methanol (80/20 $CO_2$/methanol). The shaded region on the diagram shows isenthalpic curves substantially parallel to the isothermal lines.

The P-T diagrams described herein can also be used to determine and depict conditions under which temperature variation due to pressure drop is minimized, minimal or non-existent. FIG. 19 show a P-T diagram having isenthalpic curves for a mobile phase composition containing 80% $CO_2$ and 20% methanol. Regions of the diagram can be selected, as exemplified by the shaded region A of FIG. 19. In region A, the isenthalpic curves are almost parallel to the isothermal lines. Within the shaded region A, the selection of any temperature as the inlet temperature can result in an minimal or insubstantial temperature change in the mobile phase due to pressure drop. In one embodiment, the conditions for operating a chromatographic separation system wherein the temperature variation is minimized can include selection of conditions, e.g., initial, final or both, corresponding to a region of the P-T diagram having one or more isenthalpic curves having an absolute slope of less than about 50, 40, 30, 20, 19, 18, 17, 16, 15, 14, 13, 12, 11, 10, 9, 8, 7, 6, 5, 4, 3, 2, 1.5, 1.4, 1.3, 1.2 or about 1.1. The values can also define a range of slopes such as about 1.1 to about 5. In another embodiment, the conditions for operating a chromatographic separation system wherein the temperature variation is minimized can include selection of conditions, e.g., initial, final or both, corresponding to a region of the P-T diagram having one or more isenthalpic curves having an absolute slope of about 1. The slope value can depend on the thermal properties of the system, e.g. the thermal conductivity, specific heat, or thermal diffusivity.

The method for estimating temperature difference due to pressure drop can also be used for determining a mobile phase composition for a chromatographic separation process in which the both the density and the temperature of the mobile phase remains substantially constant as the mobile phase pressure varies. That is, in this embodiment, both the temperature and the density remains substantially constant as the mobile phase pressure varies. In this embodiment, a P-T phase diagram having both isopycnic curves and isenthalpic curves are provided. In one embodiment, the P-T phase diagram containing isopycnic curves corresponding to different mobile phase compositions can first be used to select a range of mobile phase compositions between two isopycnic curves having a maximum variation in density of a mobile phase composition. The maximum variation in density can be less than about 1.0, 0.9, 0.8, 0.7, 0.6, 0.5, 0.4, 0.3, 0.2, 0.1, 0.05 or 0.02 g/L. These values can also be used to define a range such as from about 0.2 to about 0.5 g/L. Thereafter, the P-T phase diagram containing isenthalpic curves can be used to select a range of mobile phase compositions between two isenthalpic curves having a maximum temperature variation. The maximum variation in temperature can be less than about 20, 19, 18, 17, 16, 15, 14, 13, 12, 11, 10, 9, 8, 7, 6, 5, 4, 3, 2, 1, 0.5 or 0.2° C. These values can also be used to define a range such as from about 5 to about 0.5° C. In other embodiments, the maximum variation in temperature using the P-T phase diagram containing isenthalpic curves can be first used, than the variation in density using the P-T phase diagram containing isopycnic curves.

In another embodiment, the present disclosure relates to a method for determining a mobile phase composition for a chromatographic separation process, wherein the density and the temperature of the mobile phase remains substantially constant as the mobile phase pressure varies, the method including providing a first P-T phase diagram comprising isopycnic curves corresponding to different mobile phase compositions; selecting a range of mobile phase compositions bounded by a first isopycnic curve and a second isopycnic curve, wherein, in a pressure interval defined by a first and a second mobile phase pressure, the maximum variation in density of any one of the mobile phase compositions in the range is less than about 0.5 g/L; providing a second P-T phase diagram comprising isenthalpic curves corresponding to a mobile phase composition selected from the range of compositions defined in step (b); and identifying a mobile phase composition from the second P-T phase diagram, wherein the estimated temperature variation of the mobile phase in the pressure interval as described herein is less than about 5.0° C.

The first and second mobile phase pressures may, for example be the column inlet and column outlet pressure, respectively. Also, a second P-T diagram having isenthalpic curves corresponding to a mobile phase composition selected from the range of compositions defined using the diagram having isopycnic curves is used to identify a mobile phase composition from the second P-T phase diagram such that the estimated mobile phase temperature variation in the pressure interval between the first and the second mobile phase pressures, estimated using the temperature triangle described above, is minimal. For example, the estimated temperature variation is less than 5° C., such that the temperature of the mobile phase remains substantially constant. In this manner a mobile phase composition can be determined which maintains substantially the same temperature and density as the mobile phase pressure varies.

In another aspect, the present disclosure also relates to methodologies and apparatus for compensating, addressing, and optimizing retention in $CO_2$-based chromatography (i.e., mobile phase includes $CO_2$) using pressure-temperature (P-T) phase diagrams of the mobile phase having isopycnic curves. Parameters affecting carbon dioxide based chromatographic separations include temperature (e.g., column temperature, mobile phase temperature, detector temperature), pressure, and flow rate. These parameters are typically pre-set and controlled during carbon dioxide based separations. For example, one or more of these parameters may be held constant over the course of a separation (i.e., isothermal) or may be changed (i.e., temperature gradient) to effect a desired separation or retention. These parameters are often monitored or controlled by sensors placed throughout the carbon dioxide based chromatographic system (e.g., pressure sensor at the pump) or by equipment designed to achieve a pre-set value (e.g., external column heater setting or pump flow rate setting).

Density of the mobile phase can be greatly affected by changes in pressure, temperature and other system operating parameters. For example, change of pressure can greatly affect the chromatography analysis in supercritical fluid chromatography (SFC) using $CO_2$ in the mobile phase—and in particular, if carried out at a temperature where the fluid is more compressible. For the same pressure drop, a change in the density of a mobile phase is greater if the operating temperature is higher.

In high pressure liquid chromatography (HPLC), the parameters such as the flow rate, the column length, and the particle size of the chromatographic bed are varied to obtain better efficiency and/or faster analysis. These changes do not affect the retention of the sample on the column, i.e., retention factor remains almost the same. Only the efficiency varies. In contrast, in $CO_2$-based chromatography, changes in one or more of these parameters can affect retention characteristics.

Changes in chromatography parameters such as flow rate, column length, and particle size of the chromatographic bed affects the pressure profile inside the column in $CO_2$-based chromatography. The extent to which the original retention characteristics can be maintained once the chromatography parameters are changed depends on how much density variation is taking place inside the column due to the change in one or more of the parameters. In accordance with embodiments herein, pressure-temperature phase diagrams having ispoycnic curves can be used to determine how much density variation there may be for a particular pressure drop at a particular temperature. At high temperatures, where the isopycnic plots show that the density variation due to pressure change is higher, significant changes in chromatographic separation can result from changes in chromatographic parameters such as flow rate. At lower temperatures, where density variation due to pressure change is less, there can be a smaller change in chromatographic separation, i.e. separation is more robust. According to embodiments herein an isopycnic plot is used to determine a region in the plot where density does not vary significantly as a result of pressure change.

Figure 20:
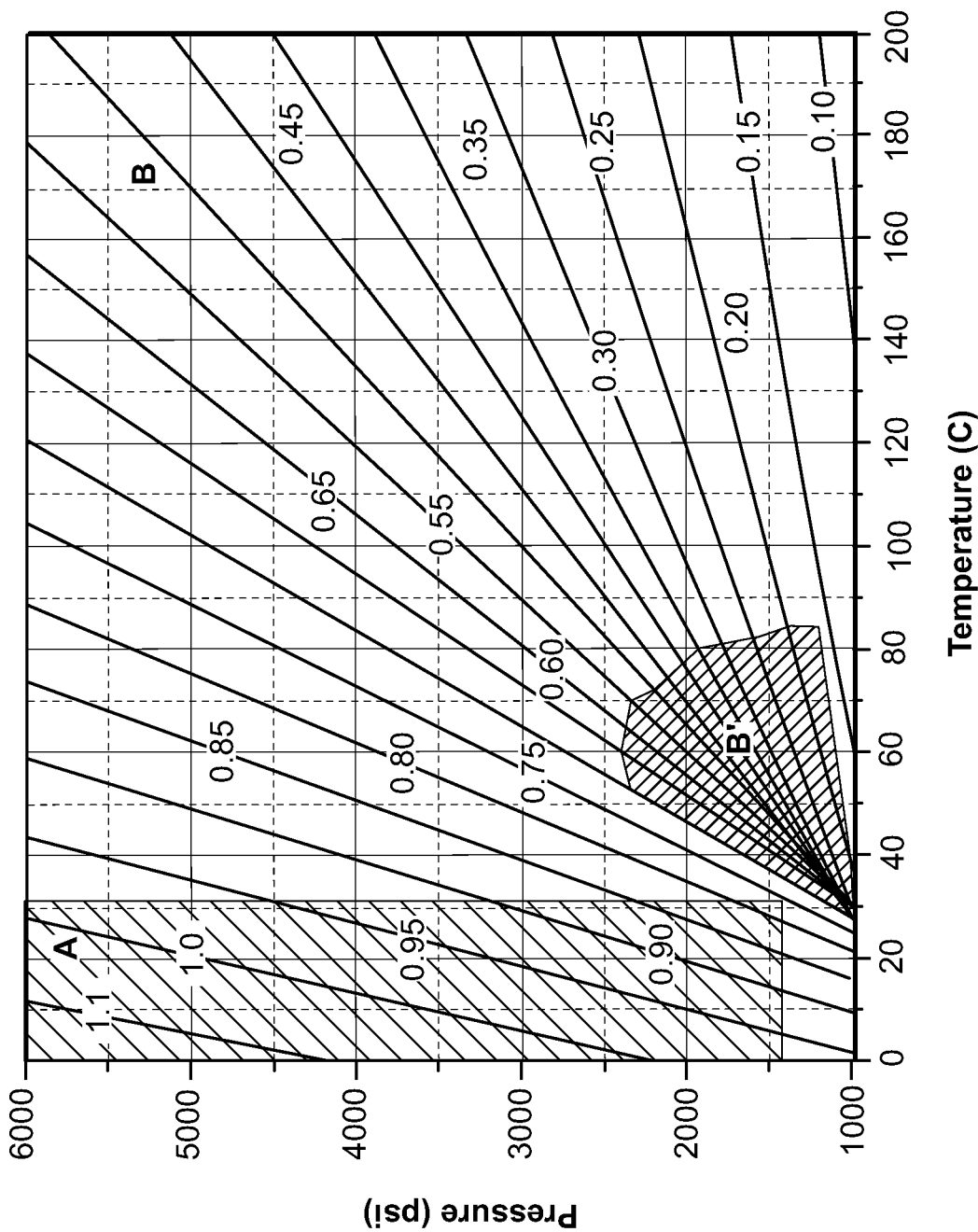
FIG. 20 is an exemplary pressure-temperature phase diagram showing isopycnic curves for a 100% carbon dioxide mobile phase. The shaded region A is an area of the diagram where the mobile phase density does not vary significantly as a result of a pressure change. The shaded region B, and more particularly B', is an area of the diagram where the mobile phase density does vary significantly as a result of a pressure change.
Figure 21:
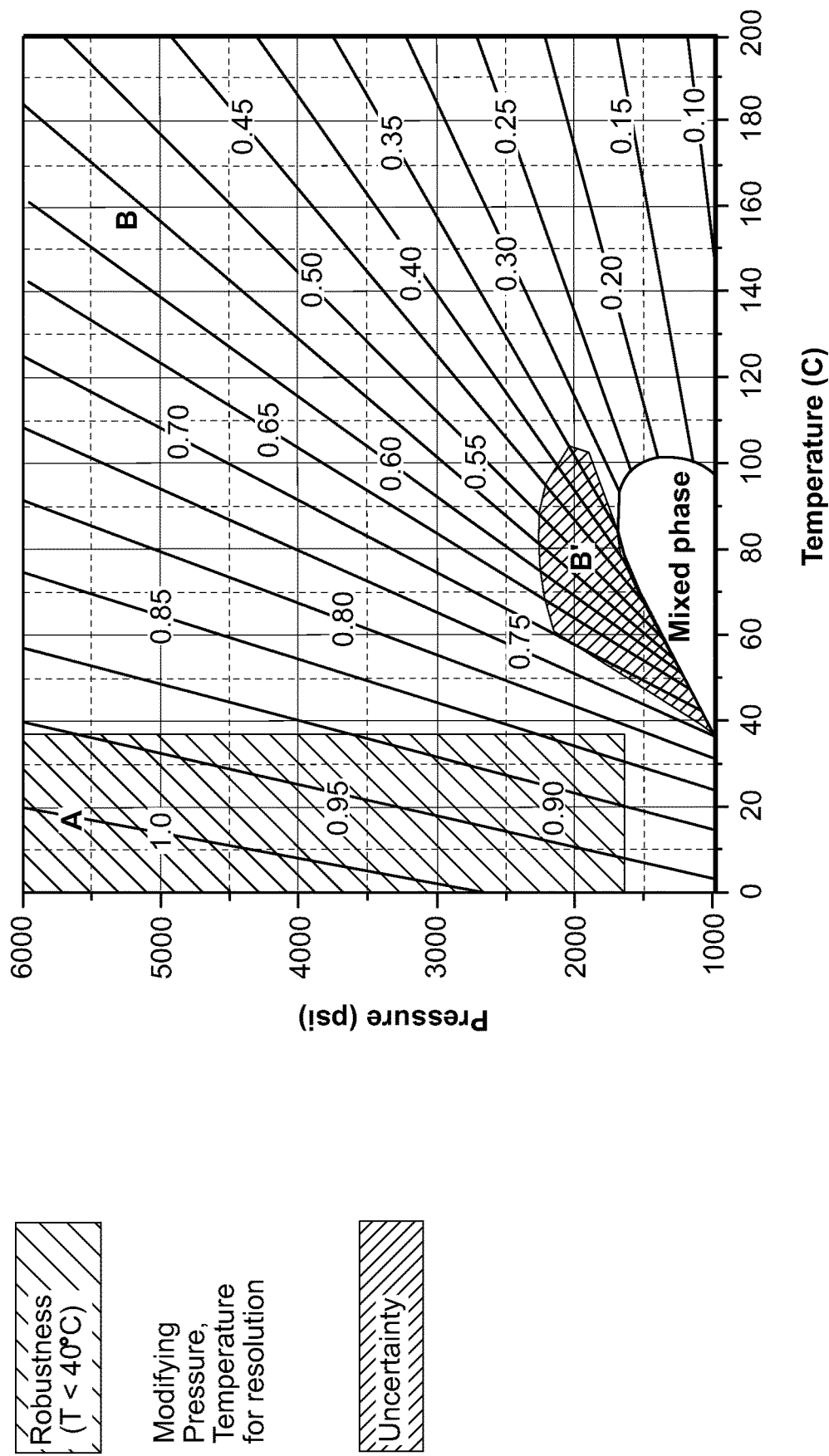
FIG. 21 is an exemplary pressure-temperature phase diagram showing isopycnic curves for a mobile phase having the composition of 90% $CO_2$ and 10% methanol (90/10 $CO_2$/methanol). The shaded region A is an area of the diagram where the mobile phase density does not vary significantly as a result of a pressure change. The shaded region B, and more particularly B', is an area of the diagram where the mobile phase density does vary significantly as a result of a pressure change.
Figure 22:
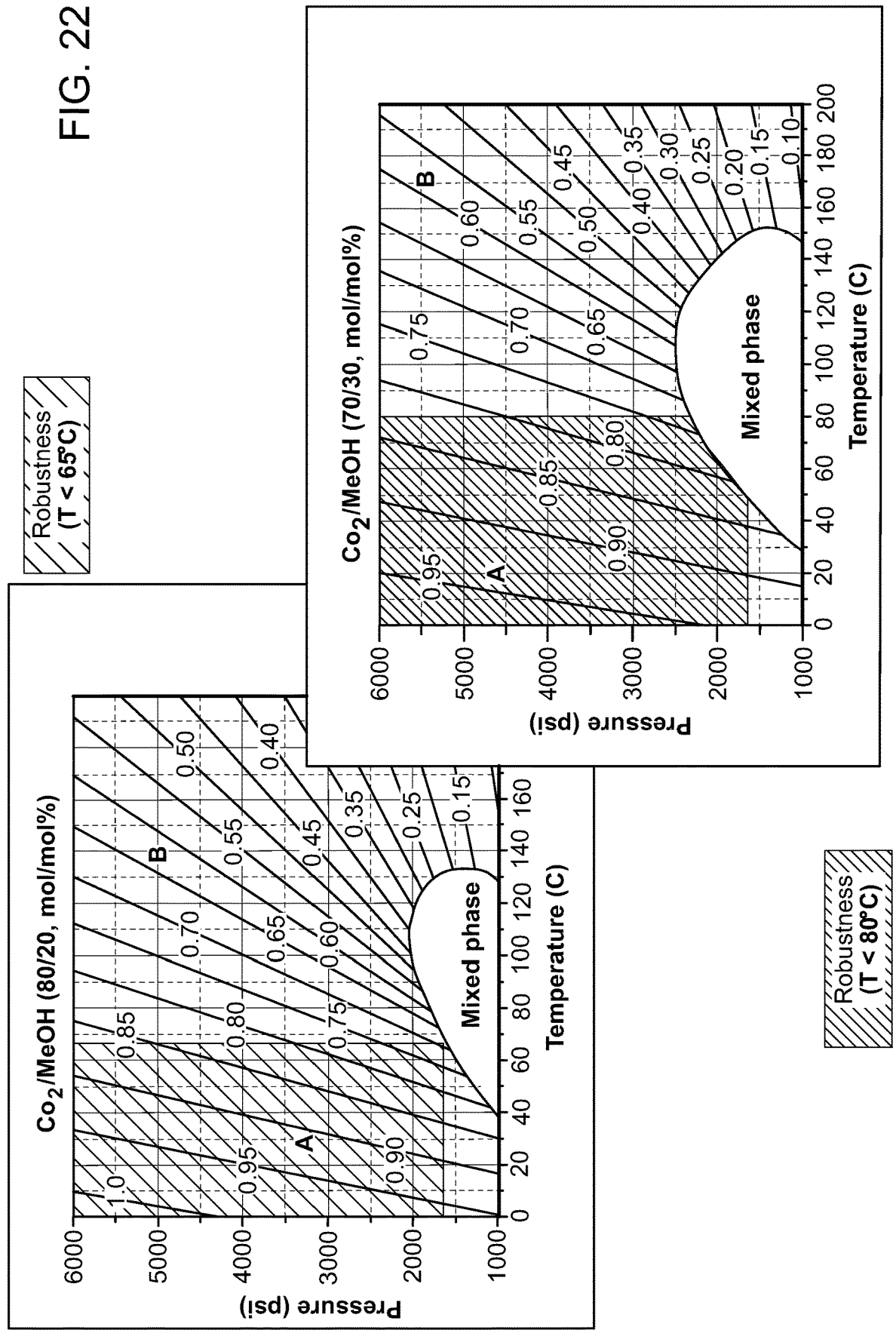
FIG. 22 is a set of two exemplary pressure-temperature phase diagram showing isopycnic curves for a mobile phase having the composition of 80% $CO_2$ and 20% methanol (80/20 $CO_2$/methanol) and a mobile phase having the composition of 70% $CO_2$ and 30% methanol (70/30 $CO_2$/methanol). The shaded regions A are areas of the diagrams where the mobile phase density does not vary significantly as a result of a pressure change. The shaded regions B are areas of the diagrams where the mobile phase density does vary significantly as a result of a pressure change.

FIGS. 20-22 show examples of isopycnic plots showing robust regions where the density does not vary significantly as a result of pressure change. FIG. 20 shows a pressure-temperature phase diagram having isopycnic curves for a 100% carbon dioxide mobile phase. The shaded region A is an exemplary area of the diagram where the mobile phase density does not vary significantly as a result of a pressure change. The shaded region B is an exemplary area of the diagram where the mobile phase density does vary significantly as a result of a pressure change. In one embodiment, the conditions for operating a chromatographic separation system wherein the temperature variation is minimized can include selection of conditions, e.g., initial, final or both, corresponding to a region of the P-T diagram having one or more isopycnic curves having an absolute slope of less than about 50, 40, 30, 20, 19, 18, 17, 16, 15, 14, 13, 12, 11, 10, 9, 8, 7, 6, 5, 4, 3, 2, 1.5, 1.4, 1.3, 1.2 or about 1.1. The values can also define a range of slopes such as about 1.1 to about 5. In another embodiment, the conditions for operating a chromatographic separation system wherein the temperature variation is minimized can include selection of conditions, e.g., initial, final or both, corresponding to a region of the P-T diagram having one or more isopycnic curves having an absolute slope of about 1. In another embodiment, the condition for operating a chromatographic separation system wherein the temperature variation is minimized can include selection of conditions, e.g., initial, final or both, corresponding to a region of one or more P-T diagrams having one or more isenthalpic and/or one or more isopycnic curves having an absolute slope for each as defined herein.

FIG. 21 shows a pressure-temperature phase diagram having isopycnic curves for a mobile phase having the composition of 90% $CO_2$ and 10% methanol (90/10 $CO_2$/methanol). The shaded region A is an area of the diagram where the mobile phase density does not vary significantly as a result of a pressure change. The shaded region B is an area of the diagram where the mobile phase density does vary significantly as a result of a pressure change.

FIG. 22 shows a set of pressure-temperature phase diagrams having isopycnic curves for a mobile phase having the composition of 80% $CO_2$ and 20% methanol (80/20 $CO_2$/methanol) and a mobile phase having the composition of 70% $CO_2$ and 30% methanol (70/30 $CO_2$/methanol). The shaded regions A are areas of the diagrams where the mobile phase density does not vary significantly as a result of a pressure change. The shaded regions B are areas of the diagrams where the mobile phase density does vary significantly as a result of a pressure change.

In one embodiment, the present disclosure relates to a method of developing a chromatographic separation process, the method including selecting a column and a mobile phase composition; providing a pressure-temperature (P-T) phase diagram of the mobile phase, wherein the phase diagram comprises isopycnic curves of the mobile phase and the pressure values range from at least 1000 to at least 6000 psi and the temperature values range from at least 0° C. to at least 200° C.; and (c) operating the chromatographic separation process in a region in the diagram where the mobile phase has a delta density/delta pressure value less than about 80% of the diagram.

The present disclosure is applicable to systems having pressures of about 100 psi, 200, 300, 400, 500, 600, 700, 800, 900, 1000, 1500, 2000, 2500, 3000, 3500, 4000, 4500, 5000, 5500, 6000, 7000, 8000, 9000 or about 10,000 psi. These values can be used to define a range, such as from about 1000 to about 6000 psi. These values can also be used to define the bounds of the P-T diagrams used to describe the mobile phase properties. Similarly, the present disclosure is applicable to systems having temperatures of about 0° C., 10, 20, 30, 40, 50, 60, 70, 80, 90, 100, 110, 120, 130, 140, 150, 160, 170, 180, 190, or about 200° C. These values can be used to define a range, such as from about 0° C. and about 200° C. These values can also be used to define the bounds of the P-T diagrams used to describe the mobile phase properties. In particular, the diagram can display mobile phase properties for pressures ranging from 1000 psi to 5000 psi, and for temperatures ranging from 0° C. and about 180° C. The pressure and temperature values disclosed herein can be used to describe the diagram display of mobile phase properties.

The chromatographic separation process can operate in a region in the diagram where the mobile phase has a delta density/delta pressure value is less than about 50%, 55%, 60%, 65%, 70%, 75%, 80%, 85%, 90%, 95% or 100% of the diagram. These values can be used to define a range, such as from about 80% to about 90%. In particular, the process can be operated in a region where the mobile phase is in a supercritical or near supercritical state.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

A improved chromatographic separation is developed using the methodology of the present disclosure. The following chromatographic system is used: an analytical scale carbon dioxide based chromatography instrument using a BEH 2-EP column (2.1×150 mm, 1.7 µm particle size), available at Waters Technologies Corporation (Milford, Mass.). The separation is isocratic using a carbon dioxide mobile phase with 5% (v/v) methanol modifier and performed at a flow rate of 2.0 mL/min. The temperature and the pressure can range from 0 to 200° C., and 1000 to 6000 psi.

Using the P-T diagram as exemplified in FIG. 2, the initial set of mobile phase conditions for temperature and pressure is selected as 70° C. and having an ABPR (Automated Back Pressure Regulator) pressure of 2000 psi. The final temperature is estimated to be about 65° C. By using the P-T diagram exemplified in FIG. 2, the possible temperature variation inside the column at 70° C. and 2000 psi ABPR pressure is non-negligible. Under these experimental conditions, thermal heterogeneity occurs inside the column and efficiency is lower than it could have been. The test solution components are separated and exhibit a first set of performance characteristics (e.g., efficiency, E1, resolution, R1, etc.).

A second set of initial mobile phase conditions for temperature and pressure is selected as 30° C. and having an ABPR (Automated Back Pressure Regulator) pressure of 1600 psi. The mobile phase composition is unchanged. The final temperature is estimated to be about 25° C. By using the P-T diagram exemplified in FIG. 2, the possible temperature variation inside the column at 30° C. and 1600 psi ABPR pressure is negligible. Under these experimental conditions, thermal heterogeneity is minimized or non-existent inside the column and efficiency is maintained. The test solution components are separated and exhibit a second set of performance characteristics (e.g., efficiency, E2, resolution, R2, etc.). Both the efficiency and the resolution are at least about 10% improved.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the technology.

What is claimed is:

1. A method for estimating temperature variation of a mobile phase passing through a column in a chromatographic separation system, the method comprising:
   providing a pressure-temperature (P-T) phase diagram of the mobile phase, wherein the phase diagram comprises isenthalpic curves of the mobile phase;
   operating a solvent delivery system module to measure a temperature of the column of the chromatographic separation system;
   operating a sample separation module to measure a mobile phase pressure of the chromatographic separation system;
   drawing a triangular figure by connecting a first, second, and a third point on the phase diagram, wherein the first point corresponds to the temperature of the column $T_{first}$ and the mobile phase pressure $P_{first}$ at a first position in the column; the second point corresponds to $T_{first}$ and to the mobile phase pressure $P_{second}$ at a second position in the column; and the third point corresponds to $P_{second}$ and $T_{second}$, wherein $T_{second}$ is the temperature of the mobile phase at the second position, wherein the first and the third points lie on the same isenthalpic curve; and,
   estimating the temperature variation by calculating the difference between $T_{first}$ and $T_{second}$.

2. The method of claim 1, wherein the second position is downstream from the first position.

3. The method of claim 2, wherein $P_{first}$ and $T_{first}$ are the pressure and temperature of the mobile phase at the entry point of the column, and $P_{second}$ and $T_{second}$ are the pressure and temperature of the mobile phase at the exit point of the column.

4. The method of claim 1, wherein the system comprises an ultra-high performance liquid chromatography system, a $CO_2$-based chromatography system, a high temperature liquid chromatography system, or a chromatography system that uses sub-critical or supercritical fluid as the mobile phase.

5. A method for improving resolution of one or more analyte peaks in a chromatographic separation process, the method comprising:
   (a) estimating the temperature variation in a first mobile phase according to claim 1; and,
   (b) obtaining a reduction in width of at least one of the one or more analyte peaks by substituting the first mobile phase with a second mobile phase having a different composition, wherein the estimated temperature variation in the second mobile phase according to claim 1 is different compared to that estimated for the first mobile phase.

6. The method of claim 5, wherein the estimated temperature variation in the second mobile phase is smaller than that estimated for the first mobile phase.

7. A method for improving resolution of one or more analyte peaks in a chromatographic separation process, the method comprising:
   (a) providing a column and a mobile phase;
   (b) estimating the temperature variation in the mobile phase between a first position and a second position in the column according to claim 1; and,
   (c) pre-cooling or pre-heating the mobile phase by a temperature equal to or less than the estimated temperature variation.

8. A method for improving resolution of one or more analyte peaks in a chromatographic separation process, the method comprising:
   (a) providing a column and a mobile phase;
   (b) estimating the temperature variation in the mobile phase between a first position and a second position in the column according to claim 1; and
   (c) cooling or heating the column at one or more positions along the length of the column during the separation process, wherein the cooling or heating results in a smaller estimated temperature variation in the mobile phase between the first and the second positions according to claim 1 than that estimated in step (b).

9. The method of claim 8, wherein the first position is the column inlet and the second position is the column outlet.

10. The method of claim 8, wherein the cooling or heating of the column at one or more positions along the length of the column results in a cooling or heating gradient that changes from the column inlet to the column outlet.

11. The method of claim 2, wherein the system comprises an ultra-high performance liquid chromatography system, a $CO_2$-based chromatography system, a high temperature liquid chromatography system, or a chromatography system that uses sub-critical or supercritical fluid as the mobile phase.

12. The method of claim 3, wherein the system comprises an ultra-high performance liquid chromatography system, a $CO_2$-based chromatography system, a high temperature liquid chromatography system, or a chromatography system that uses sub-critical or supercritical fluid as the mobile phase.

* * * * *